US009895470B2

(12) United States Patent
Li et al.

(10) Patent No.: US 9,895,470 B2
(45) Date of Patent: Feb. 20, 2018

(54) NON-FOULING, ANTI-MICROBIAL, ANTI-THROMBOGENIC GRAFT—FROM COMPOSITIONS

(75) Inventors: Jun Li, Brookline, MA (US); Trevor Squier, Peabody, MA (US); Zheng Zhang, Cambridge, MA (US); Chad Huval, Somerville, MA (US); William Shannan O'Shaughnessy, Boston, MA (US); Michael Hencke, Cambridge, MA (US); Michael Bouchard, Wyomissing, PA (US); Christopher R. Loose, Cambridge, MA (US)

(73) Assignee: Semprus Biosciences Corp., Cambridge, MA (US)

( * ) Notice: Subject to any disclaimer, the term of this patent is extended or adjusted under 35 U.S.C. 154(b) by 2211 days.

(21) Appl. No.: 12/632,686

(22) Filed: Dec. 7, 2009

(65) Prior Publication Data

US 2010/0152708 A1 Jun. 17, 2010

Related U.S. Application Data

(60) Provisional application No. 61/120,285, filed on Dec. 5, 2008, provisional application No. 61/120,292, filed
(Continued)

(51) Int. Cl.
*A61L 33/06* (2006.01)
*A61L 27/34* (2006.01)
(Continued)

(52) U.S. Cl.
CPC .............. *A61L 33/06* (2013.01); *A61L 27/34* (2013.01); *A61L 27/50* (2013.01); *A61L 29/085* (2013.01);
(Continued)

(58) Field of Classification Search
CPC ....................................................... A61L 33/06
See application file for complete search history.

(56) References Cited

U.S. PATENT DOCUMENTS

| 4,098,728 A | 7/1978 | Rosenblatt |
| 4,211,227 A | 7/1980 | Anderson et al. |

(Continued)

FOREIGN PATENT DOCUMENTS

| EP | 0479245 A2 | 4/1992 |
| JP | 2001-337298 A | 12/2001 |

(Continued)

OTHER PUBLICATIONS

Bell et al., Biomedical membranes from hydrogels and interpolymer complexes, Biopolymers II, 1995, 122, 1250175.
(Continued)

*Primary Examiner* — Paul Dickinson
(74) *Attorney, Agent, or Firm* — Baker and Hostetler LLP

(57) ABSTRACT

Substrates, optionally coated with an undercoating layer, having grafted there from one or more non-fouling materials are described herein. The non-fouling, polymeric material can be grafted from a variety of substrate materials, particularly polymeric substrates and/or polymeric undercoating layers. The graft-from techniques described herein can result in higher surface densities of the non-fouling material relative to graft-to formulations. Graft-from methods can be used to produce covalently tethered polymers. The compositions described herein are highly resistant protein absorption, particularly in complex media and retain a high degree of non-fouling activity over long periods of time. The compositions described herein may also demonstrate anti-microbial and/or anti-thrombogenic activity. The non-fouling material can be grafted from the substrate, or optionally from an undercoating layer on the substrate, preferably
(Continued)

without significantly affecting the mechanical and/or physical properties of the substrate material.

24 Claims, 1 Drawing Sheet

Related U.S. Application Data on Dec. 5, 2008, provisional application No. 61/120,312, filed on Dec. 5, 2008, provisional application No. 61/231,346, filed on Aug. 5, 2009.

(51) Int. Cl.

| | | |
|---|---|---|
| *A61L 27/50* | (2006.01) | |
| *A61L 29/08* | (2006.01) | |
| *A61L 29/14* | (2006.01) | |
| *A61L 31/10* | (2006.01) | |
| *A61L 31/14* | (2006.01) | |
| *C07H 23/00* | (2006.01) | |
| *C09D 5/16* | (2006.01) | |
| *C09D 151/00* | (2006.01) | |
| *C09D 151/06* | (2006.01) | |
| *C09D 151/08* | (2006.01) | |
| *C08L 75/04* | (2006.01) | |
| *C08L 25/08* | (2006.01) | |

(52) U.S. Cl.
CPC ............... *A61L 29/14* (2013.01); *A61L 31/10* (2013.01); *A61L 31/14* (2013.01); *C07H 23/00* (2013.01); *C09D 5/1637* (2013.01); *C09D 151/003* (2013.01); *C09D 151/06* (2013.01); *C09D 151/08* (2013.01); *C09D 151/085* (2013.01); *C08L 25/08* (2013.01); *C08L 75/04* (2013.01); *Y10T 428/31507* (2015.04); *Y10T 428/31511* (2015.04); *Y10T 428/31529* (2015.04); *Y10T 428/31663* (2015.04); *Y10T 428/31678* (2015.04); *Y10T 428/31681* (2015.04); *Y10T 428/31692* (2015.04); *Y10T 442/2525* (2015.04)

(56) References Cited

U.S. PATENT DOCUMENTS

| | | | |
|---|---|---|---|
| 4,636,208 | A | 1/1987 | Rath |
| 5,180,375 | A | 1/1993 | Feibus |
| 5,739,236 | A | 4/1998 | Bowers et al. |
| 5,844,016 | A | 12/1998 | Sawhney et al. |
| 5,866,113 | A | 2/1999 | Hendriks et al. |
| 6,054,504 | A | 4/2000 | Dalla Riva Toma |
| 6,150,459 | A | 11/2000 | Mayes et al. |
| 6,358,557 | B1 | 3/2002 | Wang et al. |
| 6,361,768 | B1 | 3/2002 | Galleguillos et al. |
| 6,387,977 | B1 | 5/2002 | Sawhney et al. |
| 6,395,800 | B1 | 5/2002 | Jones et al. |
| 6,489,382 | B1* | 12/2002 | Giesecke et al. .............. 524/89 |
| 6,558,734 | B2 | 5/2003 | Koulik et al. |
| 6,559,242 | B1 | 5/2003 | Ball et al. |
| 6,589,665 | B2 | 7/2003 | Chabrecek et al. |
| 6,711,879 | B2 | 3/2004 | Korteweg et al. |
| 6,844,028 | B2 | 1/2005 | Mao et al. |
| 7,087,658 | B2 | 8/2006 | Swan et al. |
| 7,220,491 | B2 | 5/2007 | Rouns et al. |
| 7,238,364 | B2 | 7/2007 | Sawhney et al. |
| 7,238,426 | B2 | 7/2007 | Jiang et al. |
| 7,276,286 | B2 | 10/2007 | Chapman et al. |
| 7,306,625 | B1 | 12/2007 | Stratford et al. |
| 7,431,888 | B2 | 10/2008 | Frechet et al. |
| 7,629,029 | B2 | 12/2009 | Mao et al. |
| 2001/0050749 | A1 | 12/2001 | Watanabe |
| 2003/0021823 | A1 | 1/2003 | Landers et al. |
| 2003/0143335 | A1 | 7/2003 | Qiu et al. |
| 2004/0253383 | A1 | 12/2004 | Belik et al. |
| 2004/0256232 | A1 | 12/2004 | Jiang et al. |
| 2006/0057180 | A1 | 3/2006 | Chilkoti et al. |
| 2006/0217285 | A1 | 9/2006 | Destarac |
| 2007/0048249 | A1 | 3/2007 | Youngblood et al. |
| 2007/0254006 | A1 | 11/2007 | Loose et al. |
| 2008/0181861 | A1 | 7/2008 | Jiang et al. |
| 2009/0155335 | A1 | 6/2009 | O'Shaughnessey et al. |
| 2009/0162662 | A1 | 6/2009 | Chang et al. |
| 2009/0197791 | A1 | 8/2009 | Balastre et al. |
| 2009/0259015 | A1 | 10/2009 | Jiang et al. |
| 2010/0072642 | A1 | 3/2010 | Broad et al. |
| 2010/0099160 | A1 | 4/2010 | Jiang et al. |

FOREIGN PATENT DOCUMENTS

| | | |
|---|---|---|
| JP | 2007-130194 A | 5/2007 |
| WO | 03/000443 A1 | 1/2003 |
| WO | 2004/100666 A1 | 11/2004 |
| WO | 2007/002493 | 1/2007 |
| WO | 2007/024393 A2 | 3/2007 |
| WO | 2007/095393 A9 | 8/2007 |
| WO | 2008/006911 | 1/2008 |
| WO | 2008-019381 A2 | 2/2008 |
| WO | 2008-083390 A2 | 7/2008 |
| WO | 2009-085096 A2 | 7/2009 |

OTHER PUBLICATIONS

Chapman et al., Polymeric thin films that resist the adsorpotion of proteins and the adhesion of bacteria, Langmuir, 2001, 17(4), 1225-1233.
Cheng et al., Zwitterionic carboxybetaine polymer surfaces and their resistance to long-term biofilm formation Biomaterials, 1009, 30(28), 5234-5240.
Cheng et al., Inhibitition of bacterial adhesion and biofilm formation on zwitterionic surfaces, Biomaterials, 2007, 28(29), 4192-4199.
Du et al., Grafted poly-(ethylene glycol) on lipid surfaces inhibits protein adsorption and cell adhesion, Biochimica et Biophysica Acta (BBA)—Biomembranes, 1997, 1326(2), 236-248.
Feng et al., Atom-transfer radical grafting polymerization of 2-Methacryloyloxyethyl Phosphorycholine from silicon wafer surfaces, Journal of Polymer Science Part A: Polymer Chemistry, 2004, 42, 2931-2942.
Goda et al., Biomimetic phosphorylcholine polymer grafting from polydimethylsiloxane surface using photo-induced polymerization, Biomaterials, 2006, 27(30), 5151-5160.
Harder et al., Molecular conformation in Oligo(ethylene glycol)-terminated self-assembled monolayers on gold and silver surfaces determines their ability to resist protein adsorption, The Journal of Physical Chemistry B, 1998, 102(2), 426-436.
Haynie et al., Antimicrobial activities of amphiphilic peptides covalently bonded to a water-insoluble resin, Antimicrobial Agents and Chemotherapy, 1995, 39(2), 301-307.
Ignatova et al., Combination of electrografting and atom-transfer radical polymerization for making the stainless steel surface antibacterial and protein antiadhesive, Langmuir, 2005, 22(1), 255-262.
Ishihara et al., Photoinduced graft polymerization of 2-methacryloyloxyethyl phosphorylcholine on polyethylene membrane surface for obtaining blood cell adhesion resistance, Colloids and Surfaces B: Biointerfaces, 2000, 18(3-4), 325-335.
Yuan et al., Improvement of blood compatibility on cellulose membrane surface by grating betaines, Colloids and Surfaces B: Biointerfaces, 2003, 30, 147-155.
Jiang et al., Blood compatibility of polyurethane suface grafted copolymerization with sulfobetaine monomer, Colloids and Surfaces B: Biointerfaces, 2004, 36(1), 27-33.
Jin et al., Protein-resistant polyurethane prepared by surface-initiated atom transfer radical grat polymerizaation (ATRgP) of water-soluble polymers: effects of main chain and side chain lengths of grafts, Colloids and Surfaces B: Biointerfaces, 2009, 70(1), 53-59.

(56) References Cited

OTHER PUBLICATIONS

Jin et al., Protein-resistant polyurethane via surface-initiated atom transfer radical polymerization of oligo(ethylene glycol) methacrylate, J Biomed Mater Res A, 2009, 91(4), 1189-1201.

Zhang et al., Chemical modification of cellulose membranes with sulfo ammonium zwitterionic vinyl monomer to improve hemocompatibility, Colloids and Surfaces B: Biointerfaces, 2003, 30, 249-257.

Kang et al., Surface modification and functionalization of electroactive polymer films via grafting of polyelectroly, polyampholyte and plymeric acids, Journal of Materials Science, 1996, 31, 1295-1301.

Wang et al., Highly efficient antifouling ultrafiltration membranes incorporating zwitterionic poly([3-(methaciyloylamino)propyl]-dimethyl(3-sulfopropyl) ammonium hydroxide), Journal of Membrane Science, 2009, 340, 164-170.

Liu et al., Grafting of Zwitterion from cellulose membranes via ATRP for improving blood compatibility, Biomacromolecules, 2009, 10(10), 2809-2816.

Massia et al., Immobilized RGD peptides on surface-grafted dextran promote biospecific cell attachment, Journal of Biomedical Materials Research, 2001, 56(3), 390-399.

Michel et al., Influence of PEG architecture on protein adsorption and conformation, Langmuir, 2005, 21(26), 12327-12332.

Yuan et al., Grafting sulfobetaine monomer onto the segmented poly(ether-urethane) surface to improve hemocompatibility, Journal of Biomaterials Science—Polymer Edition, 2002, 13, 1081-1092.

Sakharov et al., Catalytic oxidative deformylation of polyethylene glycols with the particpation of molecular oxygen, Kinetics Catalysis, 2001, 42, 662-668.

Yuan et al., Platelet adhesion onto segmented polyurethane surfaces modified by carboxybetaine, Journal of Biomaterials Science—Polymer Edition, 2003, 14(12), 1339-1349.

Yuan et al., Polyurethane vascular catheter surface grafted with zwitterionic sulfobetaine monomer activated by ozone, Colloids and Surfaces B: Biointerfaces.

Yuan et al., Chemical graft polymerization of sulfobetaine monomer on polyurethane surface of reduction in platelet adhesion, Colloids and Surfaces B: Biointerfaces, 2004, 39(1-2), 87-89.

Yuan et al., Surface modification of SPEC films by ozone induced graft copolymerization to improve hemocompatibility, Colloids and Surfaces B: Biointerfaces, 2003, 29, 247-256.

Zhang et al., Nonfouling behavior of polycarboxybetaine-grafted surfaces: Structural and environmental effects, Biomacromolecules (ACS Publications), retrieved Sep. 12, 2008, 10, 2686-2692.

Zhang et al., Blood compatibility of surfaces with superlow protein adsorption, Biomaterials, 2008, 29(320, 4285-4291.

Jiang, Zwitterionic Separation Materials for Liquid Chromatography and Capillary Electrophoresis Synthesis, Characterization and Application for Inorganic Ion and Biomolecule Separations, PhD Dissertation, Umåa University, Umeå, Sweden, 63 pages, 2012.

International Search Report issued in PCT/US09/67013 dated Jun. 14, 2010, 4 pages.

Jun, et al., "Surface modification of segmented poly(ether urethane) by grafting sulfo ammonium zwitterionic monomer to improve hemocompatibilities," Colloids and Surfaces B: Biointerfaces, 28(1):1-9 (2003).

Kildal, et al., "Peroxide-initiated grafting of acrylamide on to polyethylene surfaces," J. Appl. Pol. Sci., 44:1893-8 (1992).

West, et al., "The biocompatibility of crosslinkable copolymer coatings containing sulfobetaines and phosphobetaines", Biomaterials, 25(7-8):1195-1204 (2004).

Zhang, et al., "Surface Grafted Sullobetaine Polymers via Atom Transfer Radical Polymerization as Superlow Fouling Coatings", Journal of Physical Chemistry B, 110:10799-10804 (2006).

Zhang, et al., "Superlow Fouling Sulfobetaine and Carboxybetaine Polymers on Glass Slides", Langmuir 22(24):10072-10077 (2006).

Bamford et al., "Studies in Polymer Surface Functionalization and Grafting for Biomedical and Other Applications", Polymer, 1994, vol. 35, No. 13, pp. 2844-2852.

\* cited by examiner

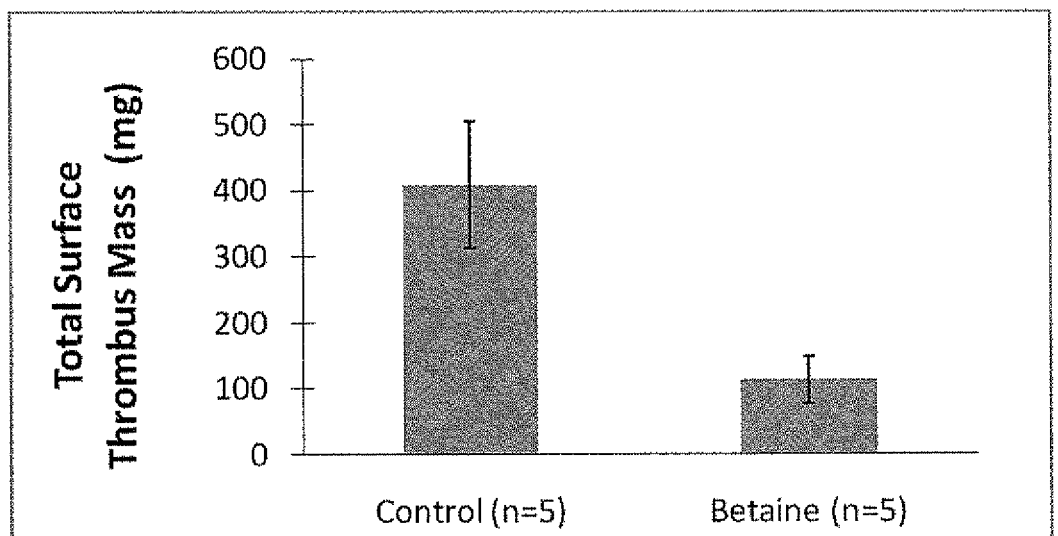

NON-FOULING, ANTI-MICROBIAL, ANTI-THROMBOGENIC GRAFT—FROM COMPOSITIONS

CROSS-REFERENCE TO RELATED APPLICATIONS

This application claimed priority to U.S. Ser. No. 61/120,285 entitled "Synthetic Anticoagulant and Antithromogenic Polymers" by Zheng Zhang, William Shannan O'Shaughnessy, Michael Hencke, Trevor Squier, and Christopher Loose, filed Dec. 5, 2008; U.S. Ser. No. 61/120,292 entitled "Presentation of Immobilized Molecules" by William Shannan O'Shaughnessy, Victoria E. Wagner Sinha, Zheng Zhang, Michael Hencke, Trevor Squier, and Christopher Loose, filed Dec. 5, 2008; U.S. Ser. No. 61/120,312 entitled "Non-Fouling, Antithrombotic Graft Coatings" by Trevor Squier, Zheng Zhang, William Shannan O'Shaughnessy, Michael Hencke, Michael Bouchard, and Christopher Loose, filed Dec. 5, 2008; and U.S. Ser. No. 61/231,346 entitled "Non-Fouling, Antithrombotic Graft Coatings" by Trevor Squier, Zheng Zhang, William Shannan O'Shaughnessy, Michael Hencke, Michael Bouchard, and Christopher Loose, filed Aug. 5, 2009.

FIELD OF THE INVENTION

The present invention is in the field of immobilized non-fouling coatings, specifically coatings that resist the adhesion of biological material and are attached to a substrate surface through a graft from method.

BACKGROUND OF THE INVENTION

Many different materials have been investigated to resist non-specific protein adsorption. Chemistries utilized for this purpose include, but are not limited to: polyethers (e.g., polyethylene glycol), polysaccharides such as dextran, hydrophilic polymers such as polyvinylpyrrolidone or hydroxyethylmethacrylate, heparin, intramolecular zwitterions or mixed charge materials, and hydrogen bond accepting groups such as those described in U.S. Pat. No. 7,276,286. The ability of these materials in preventing protein adsorption varies greatly between the chemistries. Of these materials, only a few resist fouling to the degree required for short-term in vivo application. However, the few materials appropriate for short-term application, when used for longer periods of time in complex media or in vivo, exhibit significant fouling or material degradation, making them unsuitable for long-term applications. Furthermore, surfaces coated with materials that resist in vivo degradation are often susceptible to a noticeable decrease in fouling resistance over time.

WO 2007/02493 describes grafting sulfobetaine and carboxybetaine from self-assembled monolayers on gold substrates or from silyl groups on glass substrates using atom transfer radical polymerization (ATRP). Gold and glass are not appropriate substrates for many medical devices used in vivo. Self-assembled monolayers, such as thiol-based monolayers, may be unstable since the thiol group is not stably bound to the substrate.

U.S. Pat. No. 6,358,557 to Wang et al. describes the graft polymerization of substrate surfaces, but not with a high density of a highly non-fouling polymeric material. A thermal initiator is used to initiate polymerization, typically at temperatures greater than 85° C. Such temperatures are generally not suitable for many medical devices, such as thin-walled polyurethane catheters. Further, the "salt out" method described is generally not suitable for grafting polymers such as zwitterionic polymers.

Jian et al., *Colloids and Surfaces B: Biointerfaces* 28, 1-9 (2003) describes the surface modification of segmented poly(ether urethane) by grafting sulf ammonium zwitterionic monomer, but not with a high density of non-fouling material. The resulting materials are not sufficiently non-fouling to be useful in medical device applications.

It is therefore an object of the invention to provide non-fouling polymeric coatings for various substrates, such as polymers and metal oxides, which retain their activity in the presence of blood proteins and/or in vivo due to improved molecular structures, and allow for cooperative action of immobilized agents and protein resistant chemistries to resist non-specific protein adsorption.

It is further an object of the present invention to provide non-fouling compositions containing a high density of non-fouling polymeric material and/or wherein the inter-polymer chain distance of the non-fouling polymeric materials decreases the penetration of fouling molecules into the non-fouling coating.

It is further an embodiment of the invention to provide graft-from methods of coating surfaces formed of biomaterials wherein the grafting is initiated from within the biomaterials to provide materials with a high density and stability of non-fouling polymer.

SUMMARY OF THE INVENTION

Substrates, optionally coated with an undercoating layer, having grafted there from one or more non-fouling materials are described herein. Non-fouling coatings with varying tether chemistry or polymer backbone chemistry provide an alternative approach to developing highly efficient, biocompatible, and bioresponsive non-fouling coatings. In one embodiment, the coatings are non-leaching. Conventional fouling resistant or non-fouling materials and surface coatings are susceptible to fouling over prolonged exposure to complex media and/or in vivo environments.

Using the chemistries described herein, non-fouling, polymeric materials can be grafted from a variety of substrate materials, particularly metal or polymeric substrates and/or polymeric undercoating layers. The resulting polymer coatings are generally thicker than self-assembled monolayer-based coatings and thus better cover the defects and irregularities in commercial biomaterials, including polymers and metals, so that non-fouling coatings are effective in complex media and/or in vivo.

Graft-from techniques can result in higher surface densities of the non-fouling material relative to graft-to formulations. High concentrations of polymerization initiator can be introduced into the substrate or the undercoating layer, for example, by swelling the substrate or undercoating layer in the presence of the initiator. High concentrations of initiator in and/or on the substrate and/or undercoating layer can provide a high density of polymer chains on the surface. In one embodiment, the density of the polymer chains on the surface is from about 0.5 µg/cm$^2$ to about 5 mg/cm$^2$, from about 1 µg/cm$^2$ to 100 µg/cm$^2$, or from about 2 µg/cm$^2$ to 50 µg/cm$^2$. In an alternative embodiment, the inter-polymer chain distance decreases the penetration of fouling materials into the coating material.

Graft-from methods can be used to produce covalently tethered polymers which present the highest uniformity of non-fouling groups and should exhibit the highest degree of non-fouling activity. The coatings can be grafted from substrates with various shapes, including tubular and porous structures.

The compositions described herein resist preferably greater than 50%, 55%, 60%, 65%, 70%, 75%, 80%, 85%, 90%, 95%, 99%, or 99.9% of the adsorption of protein from solution, for example phosphate buffered saline (PBS) containing protein, media, serum, or in vivo relative to an uncoated control for 1 day, 7 days, 14, 21, 30, 45, 60, 90, 120, 180, 365, or 1000 days.

The compositions described herein are stable over extended periods of time, retaining at least 25%, 30%, 35%, 40%, 45%, 50%, 55%, 60%, 65%, 70%, 75%, 80%, 85%, 90%, 95%, or 99% of their non-fouling, anti-thrombotic, and/or antimicrobial properties in PBS containing protein, media, serum, or in vivo for extended periods of time, for example, at least 1, 7, 14, 21, 30, 45, 60, 90, 120, 180, 365, or 1000 days.

The non-fouling material can be grafted from the substrate, or optionally from an undercoating layer on the substrate, without significantly affecting the mechanical and/or physical properties of the substrate material. In one embodiment, the tensile strength, modulus, device dimensions, or combinations thereof of the coated substrate are within 20%, preferably within 10%, more preferably within 5%, most preferably within 1% of the tensile strength, modulus, device dimensions, or combinations thereof of the uncoated substrate.

BRIEF DESCRIPTION OF THE DRAWINGS

FIG. 1 is a graph showing the total surface thrombus mass (mg) for UV carboxybetaine-coated Tecoflex rods and uncoated Tecoflex rods.

DETAILED DESCRIPTION OF THE INVENTION

I. Definitions

"Zwitterion" or "zwitterionic material" refers to a macromolecule, material, or moiety possessing both cationic and anionic groups. In most cases, these charged groups are balanced, resulting in a material with zero net charge. Zwitterionic polymers may include both polyampholytes (e.g, polymers with the charged groups on different monomer units) and polybetaine (polymers with the anionic and cationic groups on the same monomer unit).

"Polymer", as used herein, includes homopolymers and copolymers. Examples of copolymers include, but are not limited to, random copolymers and block copolymers.

"Antimicrobial" as used herein, refers to molecules and/or compositions that kill (i.e., bactericidal), inhibit the growth of (i.e., bacteristatic), and/or prevent fouling by, microorganisms including bacteria, yeast, fungi, mycoplasma, viruses or virus infected cells, cancerous cells, and/or protozoa.

Antimicrobial activity with respect to bacteria may be quantified using a colonization assay pre-incubation with 50% fetal bovine serum for 18-20 hours at 120 RPM at 37° C., which is preferred. Following pre-incubation, samples are placed in *Staphylococcus aureus* (*S. aureus*, ATCC 25923) which has been diluted from an overnight culture to a planktonic concentration of $1-3\times10^5$ CFU/mL in 1% tryptone soy broth (TSB). Samples are incubated with bacteria for 24-26 hrs with agitation (120 rpm) at 37° C. The concentration of TSB can vary with the organism being used. After incubation, the samples are placed in 3 ml PBS for 5 min at 240 RPM at 37° C. to remove bacteria not tightly attached. Then accumulated bacteria on materials are removed by sonication in a new solution of PBS and the total number of bacterial cells quantified through dilution plating. Preferably at least a 1, 2, 3 or 4 log reduction in bacterial count occurs relative to colonization on a control. Similar adherence assays are known in the art for assessing platelet, cell, or other material adhesion to the surface. A surface that has a lower bacterial count on it than on reference polymers may be said to reduce microbial colonization.

"Anti-thrombogenic", as used herein, refers to the ability of a composition to resist thrombus formation. Anti-thrombogenic activity can be evaluated using ex-vivo flow loop model of thrombosis. Briefly, up to 10 liters of fresh blood are collected from a single animal. This blood is heparinised to prevent coagulation, filtered to remove particulates, and autologous radiolabeled platelets are added. Within eight hours after blood harvesting, coated and uncoated substrates are placed in a flow loop circuit, which pumps blood from a bath over the substrate and then back into the bath. A second internal flow loop circuit can be established for substrate containing a lumen by connecting the two ports of the substrate through a 2nd peristaltic pump. Blood is pumped in the outer circuit at a rate of approximately 2.5 L/min, while blood in the inner circuit is pumped at a rate of approximately ~200-400 ml/min. After two hours, the substrates are removed, inspected visually for thrombus formation, and adhered platelets quantified using a Gamma counter. For samples not containing a lumen, only an outer circuit may be used to measure thrombus on the outside of the device.

"Adhesion", as used herein, refers to the non-covalent or covalent attachment of proteins, cells, or other substances to a surface. The amount of adhered substance may be quantified for proteins using the assay for non-fouling activity or for bacteria with the assay for antimicrobial activity or other relevant assays.

"Bioactive agent" or "active agent" or "biomolecule", used here synonymously, refers to any organic or inorganic therapeutic, prophylactic or diagnostic agent that actively or passively influences a biological system. For example, a bioactive agent can be an amino acid, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be proteins, glycoproteins, peptides, oligliopeptides, polypeptides, inorganic compounds, organometallic compounds, organic compounds or any synthetic or natural, chemical or biological compound.

"Non-fouling", as used herein, means that the composition reduces or prevents the amount of adhesion of proteins, including blood proteins, plasma, cells, tissue and/or microbes to the substrate relative to the amount of adhesion to a reference polymer such as polyurethane. Preferably, a device surface will be substantially non-fouling in the presence of human blood. Preferably the amount of adhesion will be decreased 20%, 25%, 30%, 35%, 40%, 45%, 50%, 55%, 60%, 70%, 75%, 80%, 85%, 90%, 95%, 99%, 99.5%, or 99.9% relative to the reference polymer.

Non-fouling activity with respect to protein, also referred to as "protein resistance" may be measured using an ELISA assay. For example, the ability of a composition to prevent the adhesion of blood proteins can be evaluated by measuring fibrinogen absorption through ELISA. Fibrinogen is a blood protein commonly used to assess the ability of a non-fouling surface to resist adsorption, given its important role in mediating platelet and other cell attachment. Briefly, samples are incubated for 90 minutes at 37° C. in 1 mg/mL fibrinogen derived from human plasma, then rinsed three times with 1×PBS and transferred to clean wells. The samples are incubated for another 90 minutes at 37° C. in 10% (v/v) fetal bovine serum to block the areas unoccupied by fibrinogen. The samples are rinsed, transferred to clean wells, and incubated for 1 hour with 5.5 ug/mL horseradish peroxidase conjugated anti-fibrinogen in 10% (v/v) fetal bovine serum. Again the samples are rinsed and transferred to clean wells with 0.1M phosphate-citrate buffer containing 1 mg/mL chromogen of o-phenylenediamine and 0.02% (v/v) hydrogen peroxide. Incubating at 37° C. for 20 minutes produces an enzyme-induced color reaction, which is terminated by the addition of 2.0N sulfuric acid. The absorbance of light intensity can then be measured using a microplate reader to determine the protein adsorption relative to controls. Preferably the amount of adhesion will be decreased at least 20%, 25%, 30%, 35%, 40%, 45%, 50%, 55%, 60%, 65%, 70%, 75%, 80%, 85%, 90%, 95%, 99%, 99.5%, or 99.9% relative to the reference polymer. For mixed protein solutions, such as whole plasma, surface plasmon resonance (SPR) or optical waveguide lightmode spectroscopy (OWLS) can be utilized to measure surface protein adsorption without necessitating the use of individual antigens for each protein present in solution. Additionally, radiolabeled proteins may be quantified on the surface after adsorption from either one protein or complex mixtures.

"Biocompatibility" is the ability of a material to perform with an appropriate host response in a specific situation. This can be evaluated using International Standard ISO 10993. Biocompatible compositions described herein are preferably substantially non-toxic. "Substantially non-toxic", as used herein, means a surface that is substantially hemocompatible and substantially non-cytotoxic.

"Substantially Non-Cytotoxic", as used herein, refers to a composition that changes the metabolism, proliferation, or viability of mammalian cells that contact the surface of the composition. These may be quantified by the International Standard ISO 10993-5 which defines three main tests to assess the cytotoxicity of materials including the extract test, the direct contact test and the indirect contact test.

"Substantially hemocompatible", as used herein, means that the composition is substantially non-hemolytic, in addition to being non-thrombogenic and non-immunogenic, as tested by appropriately selected assays for thrombosis, coagulation, and complement activation as described in ISO 10993-4.

"A substantially non-hemolytic surface", as used herein, means that the composition does not lyse 50%, preferably 20%, more preferably 10%, even more preferably 5%, most preferably 1%, of human red blood cells when the following assay is applied: A stock of 10% washed pooled red blood cells (Rockland Immunochemicals Inc, Gilbertsville, Pa.) is diluted to 0.25% with a hemolysis buffer of 150 mM NaCl and 10 mM Tris at pH 7.0. A 0.5 cm$^2$ antimicrobial sample is incubated with 0.75 ml of 0.25% red blood cell suspension for 1 hour at 37° C. The solid sample is removed and cells spun down at 6000 g, the supernatant removed, and the OD414 measured on a spectrophotometer. Total hemolysis is defined by diluting 10% of washed pooled red blood cells to 0.25% in sterile deionized (DI) water and incubating for 1 hour at 37° C., and 0% hemolysis is defined using a suspension of 0.25% red blood cells in hemolysis buffer without a solid sample.

"Complex media", as used herein, refers to biological fluids or solutions containing proteins or digests of biological materials. Examples include, but are not limited to, cation-adjusted Mueller Hinton broth, tryptic soy broth, brain heart infusion, or any number of complex media, as well as any biological fluid.

"Biological fluids" are fluids produced by organisms containing proteins and/or cells, as well as fluids and excretions from microbes. This includes, but is not limited to, blood, saliva, urine, cerebrospinal fluid, tears, semen, and lymph, or any derivative thereof (e.g., serum, plasma).

"Brushes" or "Polymer Brushes" are used herein synonymously and refer to polymer chains that are bound to a surface generally through a single point of attachment. The polymers can be end-grafted (attached via a terminal group) or attached via a side chain or a position in the polymer chain other than a terminal position. The polymers can be linear or branched. For example, the polymer chains described herein can contain a plurality of side chains that contain zwitterionic groups. The side chains can consist of a single non-fouling moiety or monomer and/or a non-fouling oligomer (e.g., 2-10 monomers) or polymer (e.g., >10 monomers).

"Branch" and "Branched tether," are used interchangeably and refer to a polymer structure which originates from a single polymer chain but terminates in two or more polymer chains. The polymer may be a homopolymer or copolymer. Branched tether polymer structures may be ordered or random, may be composed, in whole or in part, of a non-fouling material, and may be utilized to immobilize one or more bioactive agents. In one embodiment, the branched tether is a dendrimer. A branched tether may be immobilized directly to a substrate or to an undercoating layer covering a substrate.

"Degradation products" are atoms, radicals, cations, anions, or molecules which are formed as the result of hydrolytic, oxidative, enzymatic, or other chemical processes.

"Density", as used herein, refers to the mass of material including, but not limited to, non-fouling materials and bioactive agents, that is immobilized per surface area of substrate.

"Inter-polymer chain distance", as used herein, refers to the distance between non-fouling polymer chains on the surface of the substrate or undercoating layer. Preferably, this distance is such that the non-fouling chains decrease the penetration of fouling materials into the coating material.

"Effective surface density", as used herein, means the range of densities suitable to achieve an intended surface effect including, but not limited to, antimicrobial or non-fouling activity, as defined herein.

"Hydrophilic" refers to polymers, materials, or functional groups which have an affinity for water. Such materials typically include one or more hydrophilic functional groups, such as hydroxyl, zwitterionic, carboxy, amino, amide, phosphate, hydrogen bond forming, and/or ether groups.

"Immobilization" or "immobilized", as used herein, refers to a material or bioactive agent that is covalently or non-covalently attached directly or indirectly to a substrate. "Co-immobilization" refers to immobilization of two or more agents.

"Non-degradable" as used herein, refers to material compositions that do not react significantly within a biological environment either hydrolytically, reductively, enzymatically or oxidatively to cleave into smaller or simpler components.

"Stable", as used herein, refers to materials which retain at least 25%, 30%, 35%, 40%, 45%, 50%, 55%, 60%, 70%, 75%, 80%, 85%, 90%, 95%, or 99% of their original material properties such as surface contact angle, non-fouling, anti-thrombogenic, and/or antimicrobial activity for a time of 1, 7, 14, 30, 90, 365, or 1000 days in PBS containing protein, media, serum, or in vivo.

"Substrate", as used herein, refers to the material on which an undercoating layer and/or non-fouling coating is applied, or which is formed all or in part of non-fouling material, or on which the non-fouling and/or antimicrobial agents are immobilized.

"Coating", as used herein, refers to any temporary, semi-permanent or permanent layer, or layers, treating or covering a surface. The coating may be a chemical modification of the underlying substrate or may involve the addition of new materials to the surface of the substrate. It includes any increase in thickness to the substrate or change in surface chemical composition of the substrate. A coating can be a gas, vapor, liquid, paste, semi-solid or solid. In addition, a coating can be applied as a liquid and solidified into a solid coating.

"Undercoating layer" refers to any coating, combination of coatings, or functionalized layer covering an entire substrate surface or a portion thereof under an additional coating.

"Non-leaching" or "Substantially non-leaching", as used herein synonymously, means that the compositions retains greater than 50%, 55%, 60%, 65%, 70%, 75%, 80%, 85%, 90%, 95%, or 99% of the immobilized coating or bioactive agent over the course of 7, 14, 30, 90, 365, or 1000 days in PBS containing protein, media, serum, or in vivo. This can be assessed using radiolabeled active agent.

"Tether" or "tethering agent" or "Linker", as used herein synonymously, refers to any molecule, or set of molecules, or polymer used to covalently immobilize one or more non-fouling materials, one or more bioactive agents, or combinations thereof on a material where the molecule remains as part of the final chemical composition. The tether can be either linear or branched with one or more sites for immobilizing bioactive agents. The tether can be any length. However, in one embodiment, the tether is greater than 3 angstroms in length. The tether may be non-fouling, such as a monomer, oligomer, or polymer or a non-fouling non-zwitterionic material. The tether may be immobilized directly on the substrate or on a polymer, either of which may be non-fouling.

"Non-naturally occurring amino acid", as used herein, refers to any amino acid that is not found in nature. Non-natural amino acids include any D-amino acids, amino acids with side chains that are not found in nature, and peptidomimetics. Examples of peptidomimetics include, but are not limited to, b-peptides, g-peptides, and d-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, exist as the D and L forms. Nearly all of the amino acids occurring in nature are the L-forms. D-forms of the amino acids are not found in the proteins of higher organisms, but are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction. Non-naturally occurring amino acids also include residues, which have side chains that resist non-specific protein adsorption, which may be designed to enhance the presentation of the antimicrobial peptide in biological fluids, and/or polymerizable side chains, which enable the synthesis of polymer brushes using the non-natural amino acid residues within the peptides as monomeric units.

"Polypeptide", "peptide", and "oligopeptide" encompasses organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e. production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

"Antimicrobial peptide" ("AmP"), as used herein, refers to oligopeptides, polypeptides, or peptidomimetics that kill (i.e., are bactericidal) or inhibit the growth of (i.e., are bacteriostatic) microorganisms including bacteria, yeast, fungi, mycoplasma, viruses or virus infected cells, and/or protozoa.

"Coupling agent", as used herein, refers to any molecule or chemical substance which activates a chemical moiety, for example on a bioactive agent or on the material to which it will be attached, to allow for formation of a covalent or non-covalent bond between the bioactive agent wherein the material does not remaining in the final composition after attachment.

"Cysteine", as used herein, refers to the amino acid cysteine or a synthetic analogue thereof, wherein the analogue contains a free sulfhydryl group.

"Membrane-targeting antimicrobial agent", as used herein, refers to any antimicrobial agent that retains its bactericidal or bacteriostatic activity when immobilized on a substrate and can therefore be used to create an immobilized antimicrobial surface. In one embodiment, the membrane-targeting antimicrobial agent is an antimicrobial peptide, and in another embodiment it is a quaternary ammonium compound or polymer. "Immobilized bactericidal activity" as used herein, refers to the reduction in viable microorganisms including bacteria, yeast, fungi, mycoplasma, viruses or virus infected cells, and/or protozoa that contact the surface. For bacterial targets, bactericidal activity may be quantified as the reduction of viable bacteria based on the ASTM 2149 assay for immobilized antimicrobials, which may be scaled down for small samples as follows: an overnight culture of a target bacteria in a growth medium such as Cation Adjusted Mueller Hinton Broth, is diluted to approximately $1 \times 10^5$ cfu/ml in pH 7.4 Phosphate Buffered Saline using a predetermined calibration between OD600 and cell density. A 0.5 cm$^2$ sample of immobilized antimicrobial surface is added to 0.75 ml of the bacterial suspension. The sample should be covered by the liquid and should be incubated at 37° C. with a sufficient amount of mixing that the solid surface is seen to rotate through the liquid. After 1 hour of incubation, serial dilutions of the bacterial suspension are plated on agar plates and allowed to grow overnight for quantifying the viable cell concentration. Preferably at least a 1, 2, 3 or 4 log reduction in bacterial count occurs relative to a control of bacteria in phosphate buffered saline (PBS) without a solid sample.

The term "alkyl" refers to the radical of saturated or unsaturated aliphatic groups, including straight-chain alkyl, alkene, and alkyne groups, branched alkyl, alkene, or alkyne groups, cycloalkyl (alicyclic), cycloalkene, and cycloalkyne groups, alkyl, alkene, or alkyne substituted cycloalkyl, cycloalkene, or cycloalkyne groups, and cycloalkyl substituted alkyl, alkene, or alkyne groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 20 or fewer carbons, more preferably less than 10 carbons atoms, most preferably less than 7 carbon atoms. Likewise, preferred cycloalkyls have from 3-10 carbon atoms in their ring structure, and more preferably have 5, 6 or 7 carbons in the ring structure.

It will be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, but are not limited to, aryl, heteroaryl, hydroxyl, halogen, alkoxy, nitro, sulfhydryl, sulfonyl, amino (substituted and unsubstituted), acylamino, amido, alkylthio, carbonyl groups, such as esters, ketones, aldehydes, and carboxylic acids; thiocarbonyl groups, sulfonate, sulfate, sulfinylamino, sulfamoyl, and sulfoxido.

The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This polymers described herein are not intended to be limited in any manner by the permissible substituents of organic compounds.

II. Compositions

A. Substrates

The non-fouling material may be grafted from a variety of different substrates or an undercoating layer immobilized on the substrate. Examples of suitable materials include, but are not limited to, metallic materials, ceramics, polymers, woven and non-woven fibers, inert materials such as silicon, and combinations thereof. In one embodiment, the substrate is a material other than gold or glass.

Suitable metallic materials include, but are not limited to, metals and alloys based on titanium, such as unalloyed titanium (ASTM F67) and titanium alloys, such as ASTM F1108, Ti-6Al-4V ELI (ASTM F136), Nitinol (ASTM F2063), nickel titanium alloys, and thermo-memory alloy materials; stainless steel (ASTM F138 and F139), tantalum (ASTM F560), palladium, zirconium, niobium, molybdenum, nickel-chrome, or certain cobalt alloys including Stellite, cobalt-chromium (Vitallium, ASTM F75 and Wrought cobalt-chromium (ASTM F90)), and cobalt-chromium-nickel alloys such as ELGILOY® and PHYNOX®.

Suitable ceramic materials include, but are not limited to, oxides, carbides, or nitrides of the transition elements such as titanium oxides, hafnium oxides, iridium oxides, chromium oxides, aluminum oxides, and zirconium oxides. Silicon based materials, such as silica, may also be used.

Suitable polymeric materials include, but are not limited to, polystyrene and substituted polystyrenes, polyalkylenes, such as polyethylene and polypropylene, poly(urethane)s, polyacrylates and polymethacrylates, polyacrylamides and polymethacrylamides, polyesters, polysiloxanes, polyethers, poly(orthoesters), poly(carbonates), poly(hydroxyalkanoate)s, polyfluorocarbons, PEEK, Teflon, silicones, epoxy resins, KEVLAR®, NOMEX®, DACRON®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof. In one embodiment the substrate is a medical grade polyurethane or CARBOTHANE®, aliphatic polycarbonate-based polyurethanes, available from Lubrizol Corporation, blended with appropriate extrusion agents and plasticizers, possibly one already approved by the FDA or other appropriate regulatory agency for use in vivo.

The substrates may optionally contain a radiopaque additive, such as barium sulfate or bismuth to aid in radiographic imaging.

Substrates may be in the form of, or form part of, films, particles (nanoparticles, microparticles, or millimeter diameter beads), fibers (wound dressings, bandages, gauze, tape, pads, sponges, including woven and non-woven sponges and those designed specifically for dental or ophthalmic surgeries), surgical, medical or dental instruments, blood oxygenators, ventilators, pumps, drug delivery devices, tubing, wiring, electrodes, contraceptive devices, feminine hygiene products, endoscopes, grafts (including small diameter <6 mm), stents (including coronary, urethral, renal, biliary, colorectal, esophageal, pulmonary, urethral, and vascular), stent grafts (including abdominal, thoracic, and peripheral vascular), pacemakers, implantable cardioverter-defibrillators, cardiac resynchronization therapy devices, cardiovascular device leads, ventricular assist devices and drivelines, heart valves, vena cava filters, endovascular coils, catheters (including central venous, peripheral central, midline, peripheral, tunneled, dialysis access, urinary, neurological, peritoneal, intra-aortic balloon pump, angioplasty balloon, diagnostic, interventional, drug delivery, etc.), catheter connectors and valves (including needleless connectors), intravenous delivery lines and manifolds, shunts, wound drains (internal or external including ventricular, ventriculoperitoneal, and lumboperitoneal), dialysis membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal, intracranial), ophthalmic devices including contact lenses, orthopedic devices (including hip implants, knee implants, shoulder implants, spinal implants (including cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, breast implants, penile implants, maxillofacial implants, cosmetic implants, valves, appliances, scaffolding, suturing material, needles, hernia repair meshes, tension-free vaginal tape and vaginal slings, prosthetic neurological devices, tissue regeneration or cell culture devices, or other medical devices used within or in contact with the body or any portion of any of these.

In one embodiment, the substrate is a vascularly inserted catheter such as a peripherally inserted central catheter (PICC), central venous catheter (CVC), or hemodialysis catheter, venous valves, punctual plugs, and intra-ocular devices and implants. In another embodiment, the substrate is a vascularly inserted catheter formed from a medical grade polyurthethane or CARBOTHANE® or formed from a material coated with a medical grade polyurethane or CARBOTHANE®.

The non-fouling materials can also be added to paints and other coatings and filters to prevent mildew, bacterial contamination, and in other applications where it is desirable to prevent fouling, such as marine applications (ship hull coatings), fuel tanks, oil pipelines, industrial piping, pharmaceutical equipment, drug delivery devices such as inhalers, contact lenses, dental implants, coatings for in vivo sensors, textiles such as hospital drapes, gowns, or bedding, ventilation conduits, doorknobs, devices for separations, such as membranes for microbial suspension, biomolecule separation, protein fractionation, cell separation, waste water treatment, water purification, bioreactors, and food processing.

These materials can also be used to treat surfaces of fibers, particulates and films for the applications of textiles, additives, electric/optical appliances, packaging materials and colorants/inks.

The substrate may contain an initiator to initiate polymerization from the surface. For example, such substrates may initially have radicals imbibed in the surface or within the substrate and may for example, initiate polymerization of polymer chains. For example, substrates, such as polyurethane, can be treated to faint radicals within and/or on the substrate.

In some embodiments, the substrate is substantially free of thiol groups; that is, the substrates do not contain a thiol moiety, such as a thiol linker. In another embodiment, the substrate may further contain an undercoating layer disposed on a surface of the substrate. Also contemplated herein is a substrate having two or more surfaces not capable of simultaneous exposure to a light source.

1. Effective Surface Area

In addition to the chemical composition of the substrate, the micro and nano structure of the substrate surface may be useful to maximize the surface area available for non-fouling material and/or antimicrobial agent attachment. For metallic and ceramic substrates, increased surface area can be created through surface roughening, for example by a random process such as plasma etching. Alternatively, the surface can be modified by controlled nano-patterning using photolithography. Polymeric substrates can also be roughened as with metallic and ceramic substrates. For alternative applications, creating a polished or smoother surface may enhance non-fouling properties of the material. The surface can be modified to enhance the attachment and stability of an undercoating coating. Alternatively, the surface may be polished or smoothed to reduce surface area as this may reduce physical features which could trap fouling agents. Further, having a defined roughness with physical features of specified sizes and distributions may control the interaction of bacteria, proteins, or other fouling agents with the surface. Each of these roughness variants may be enhanced with the addition of a non-fouling coating.

2. Surface Microstructure

In the case where a greater density of non-fouling material is desired, the creation of microstructure on the substrate surface can create more area for grafting non-fouling materials from the surface, without increasing the apparent surface area of the substrate. For polymeric substrates, including hydrogel networks, this surface morphology can be created through appropriate polymer structural design. One example of this methodology is the growth of surface tethered dendrimeric polymers. Each generation of the dendrimer effectively doubles the number of zwitterionic sites presenting. Other polymer architectures include brush polymers, such as brush copolymers, comb polymers, such as comb copolymers, linear and branched copolymers, cross-linked polymers, hydrogels, polymer blends, and combinations thereof.

B. Non-Fouling Materials

Surfaces which resist non-specific protein adsorption are important in the development of biomedical materials, such as medical devices and implants. Such coatings limit the interactions between the implants and physiological fluids. In environments where fluids contain high concentrations of biological proteins, such as blood contacting applications, prevention of protein adsorption may prevent fouling of the device surface and/or thrombus formation.

1. Zwitterionic Materials

Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer contains a phosphorylcholine moiety, a sulfobetaine moiety, a carboxy betaine moiety, derivatives thereof, or combinations thereof. Substrate surfaces treated with phosphorylcholine (PC), a natural zwitterionic molecule, not only exhibit reduced protein adsorption, but also exhibit increased blood compatibility, when compared to untreated substrate surfaces. Polymers created from phosphorylcholine are also considered biomimetic in addition to exhibiting the properties discussed above.

Sulfobetaine, closely resembles 2-aminoethanesulfonic acid, one of the most abundant, low molecular weight organic compounds found in animals. Sulfobetaine monomers are typically easier to handle than phosphorylcholine and the resulting polymers are generally easier to synthesize than the corresponding phosphorylcholine analogs.

Polycarboxybetaines are polymeric analogs of the naturally occurring zwitterion, glycine betaine. Similar to polyphosphorylcholines and polysulfobetaines, polycarboxybetaines are another class of zwitterionic, biomimetic polymers with exceptional resistance to biofouling. These polymers are particularly well suited for blood contacting applications due to anti-thrombogenic and anticoagulant properties unique to carboxybetaines. In addition to these properties, it is possible to design carboxybetaine monomers such that the resulting polymers contain reactive functional groups for immobilization of bioactive molecules. By creating carboxybetaine brushes on the surface, the dual function of resisting protein or platelet attachment and having an actively anticoagulant group may reduce thrombosis on a surface further than using either strategy alone.

Polysulfo- and polycarboxybetaines are not only biomimetic and highly resistant to bacterial adhesion, biofilm formation, and nonspecific protein adsorption from blood serum and plasma, they are also non-toxic, biocompatible and typically exhibit greater stability in complex media or in vivo when compared to both polyphosphorylcholine and poly(ethylene glycol), which may be degraded. The application of these materials and coatings can be further extended using biologically active agents, such as antimicrobial peptides.

Other natural and synthetic zwitterion chemistries can be used to design non-fouling materials for the biomedical applications described herein. Some examples of natural zwitterions chemistries that could be used for non-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create non-fouling materials, include, but are not limited to, amino-carboxylic acids (carboxy betaines), amino-sulfonic acids (sulfa betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, or at the terminal groups.

Materials containing, or composed of, these natural or synthetic zwitterions, can be applied to surfaces, particularly the surfaces of medical devices, in order to improve biocompatibility, reduce thrombogenesis (such as on the surface of stents or venous valves), and reduce fouling by proteins or bacteria present in solution. This is particularly applicable for surfaces where non-specific binding of proteins in solution could negatively impact the desired or necessary mechanics of a device.

In one embodiment, the non-fouling material is a zwitterionic polymer grafted from the substrate. For example, the polymer can contain one or more monomers of Formula I:

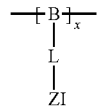

wherein B is selected from the group consisting of:

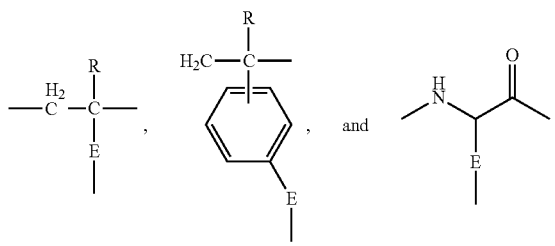

wherein R is selected from the group consisting of hydrogen, substituted alkyl, or unsubstituted alkyl;

E is selected from the group consisting of substituted alkyl, unsubstituted alkyl, —(CH$_2$)$_y$C(O)O—, and —(CH$_2$)$_y$C(O)NR$^2$;

Y is an integer from 0-12;

L is absent or is a straight or branched alkyl group optionally including one or more oxygen atoms;

ZI is a zwitterionic group; and

X is an integer from 3 to 1000.

In a particular embodiment, ZI is selected from the group consisting of

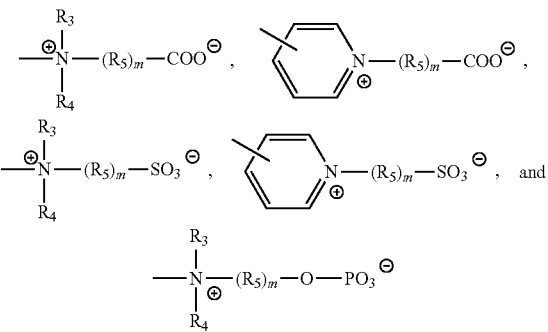

wherein R$_3$ and R$_4$ are independently selected from the group consisting of hydrogen and substituted or unsubstituted alkyl;

R$_5$ is selected from the group consisting of substituted or unsubstituted alkyl, phenyl, and polyether groups; and M is an integer from 1-7.

In another embodiment, the polymer contains one or more monomers of Formula II:

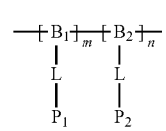

wherein B$_1$ and B$_2$ are independently selected from

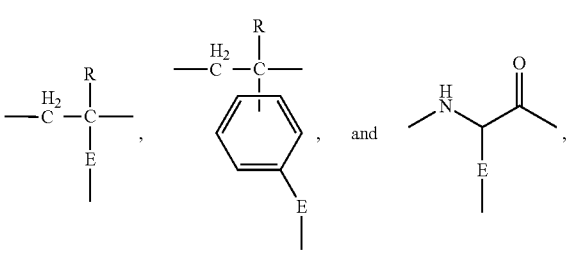

R is selected from hydrogen and substituted or unsubstituted alkyl;

E is selected from substituted or unsubstituted alkylene, —(CH$_2$)$_p$C(O)O—, and —(CH$_2$)$_p$C(O)NR$^2$—, wherein p is an integer from 0 to 12, R$^2$ is selected from hydrogen and substituted or unsubstituted alkyl;

L is a straight or branched alkylene group optionally including one or more oxygen atoms;

P$_1$ is a positively charged group;

P$_2$ is a negatively charged group, such as a carboxylate group or an SO$_3^-$ group;

m is an integer from 3 to 1000; and n is an integer from 3 to 1000.

In one embodiment, the positively charged group is a moiety containing a quaternary nitrogen or a cationic phosphorous group and the negatively charged group is a moiety containing a carboxylic acid group, SO$_3^-$, or PO$_3^-$ group.

In still another embodiment, the polymer contains one or monomers of Formula III, IV, or V:

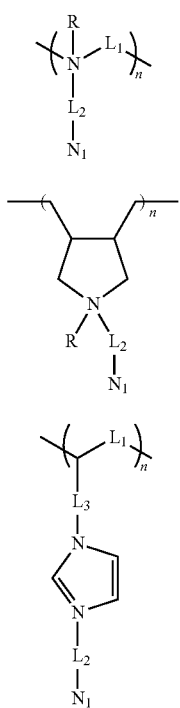

wherein R is selected from and substituted or unsubstituted alkyl;

L$_1$ L2, and L$_3$ are independently a straight or branched alkylene group optionally including one or more oxygen atoms; and n is an integer from 3 to 1000; and N1 is a negatively charged group such as a carboxylate group, SO$_3^-$ group, or PO$_3^-$ group.

In one embodiment, the non-fouling material is a polymer containing monomers derived from sulfobetaine or carboxybetaine. Examples of monomers include sulfobetaine methacrylate (SBMA) or carboxybetaine methacrylate (CBMA). Examples of such polymers include, but are not limited to, poly(carboxy betaine methacrylate) (polyCBMA) and poly(sulfobetaine methacrylate) (polySBMA). In another embodiment, the non-fouling material polymer is a polymer containing CBMA or SBMA and one or more additional monomers. The additional monomers can be zwitterionic or non-zwitterionic monomers.

In certain embodiments, an antimicrobial and/or anti-thrombotic composition is provided, that contains a substrate, for example, polyurethane, covalently bound to a plurality of polymer chains. For example, such polymer chains may be represented by Formula I, II, III, IV, or V. In certain embodiments, the non-fouling material is a brush structure containing one or more monomers of Formula I, II, III, V, or V. In still other embodiments, a the non-fouling material is a copolymer containing one or more of the monomers represented by Formula I, II, III, IV, or V.

In some embodiments, the compositions are antimicrobial compositions containing a polymeric substrate and a zwitterionic polymer, covalently bound to the polymeric substrate. The zwitterionic polymer may be formed by initiating polymerization with radicals present in the polymeric substrate, in the presence of one or more monomers, such as sulfobetaine methacrylate or carboxybetaine methacrylate monomers.

Also provided herein is a composition containing a zwitterionic polymer covalently bound to a polymeric substrate, wherein the polymeric composition has improved non-fouling, antimicrobial, and/or anti-thrombotic activity compared to a polymer formed from mixtures of zwitterionic and non-zwitterionic monomers. In another embodiment, a polymeric composition is provided that includes a zwitterionic polymer covalently bound to a polymeric substrate, wherein the composition exhibits improved non-fouling, antimicrobial, and/or anti-thrombotic activity as compared to a composition having a zwitterionic polymer bound to a self-assembled monolayer immobilized on the substrate through a thiol moiety.

2. Non-Zwitterionic Materials

The non-fouling coating can also contain a non-zwitterionic non-fouling material, alone or in combination with a zwitterionic material. These non-fouling groups may have varying degrees of non-fouling performance in a range of environments. Suitable non-zwitterionic materials include, but are not limited to, polyethers, such as polyethylene glycol, poly(ethylene oxide-co-propylene oxide) (PEO-PPO) block copolymers, polysaccharides such as dextran, hydrophilic polymers such as polyvinylpyrrolidone (PVP) and hydroxyethylmethacrylate (HEMA), acrylonitrile-acrylamide copolymers, heparin, mixed charge materials, and materials containing hydrogen bond accepting groups, such as those described in U.S. Pat. No. 7,276,286. Suitable polymer structures included, but are not limited to, polymers or copolymers containing monomers of Formula I wherein ZI is replaced by a non-zwitterionic, non-fouling headgroup.

3. Co-Monomers

The non-fouling polymers grafted from the surface of the substrate can be a copolymer, such as a random or block copolymer. Suitable comonomers include, but are not limited to, acrylates, acrylamides, vinyl compounds, multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams, and combination thereof. Exemplary monomers are listed below:

(1) Charged methacrylates or methacrylates with primary, secondary or tertiary amine groups, such as, 3-sulfopropyl methacrylate potassium salt, (2-dimethylamino)ethyl methacrylate) methyl chloride quaternary salt, [2-(methacryloyloxy)ethyl]trimethyl-ammonium chloride, methacryloyl chloride, [3-(methacryloylamino)propyl]-trimethylammonium chloride), 2-aminoethyl methacrylate hydrochloride, 2-(diethylamino)ethyl methacrylate, 2-(dimethylamino) ethyl methacrylate, 2-(tert-butylamino) ethyl methacrylate, and 2-(tert-butylamino-ethyl methacrylate.

(2) Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

(3) Reactive or crosslinkable methacrylates, such as 2-(trimethylsilyloxy)ethyl methacrylate, 3-(trichlorosilyl)propyl methacrylate, 3-(trimethoxysilyl)propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate 3-(dimethylchlorosilyl)propyl methacrylate 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

(4) Other methacrylates, such as ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate.

Condensation type monomers may also be used.

Acrylamide and/or methacrylamide derivatives of the monomers listed above can also be used, as well as other monomers with unsaturated bonds.

Multifunctional monomers, such di, tri, or tetraacrylates can be used to form highly branched structures which can provide a higher concentration of non-fouling groups on the surface.

4. Density of Non-Fouling Materials

Having increased density of non-fouling chains may improve non-fouling performance. Reducing inter-chain distance, which may improve performance, may be accomplished by having a denser concentration of initiator. This may be accomplished by imbibing initiator into the substrate or having an undercoating that serves as or incorporates a high density of initiator. Longer polymer chains and/or branched non-fouling chains may further improve performance.

In one embodiment, the surface has a high density of polymer chains on the surface. In one embodiment, the density of the polymer chains on the surface is from about 0.5 µg/cm$^2$ to about 5 mg/cm$^2$, from about 1 ug/cm$^2$ to 100 ug/cm$^2$, or from about 2 ug/cm$^2$ to 50 ug/cm$^2$. In an alternative embodiment, the inter-polymer chain distance is such that it decreases the penetration of fouling materials into the coating material, for example, <5 nm, <10 nm, <50 nm, or <100 nm.

C. Fluorescent and Colormetric Labels

In one embodiment, the surface is stained or labeled with one or more colorimetric labels, fluorescence labels, or combinations thereof. These labels are used to visualize the surface using the naked eye, spectroscopy, microscopy, or combinations thereof. Suitable microscopy techniques include, but are not limited to, optical microscopy, fluorescent microscopy, and combinations thereof.

The surface can be stained through a chemical reaction or by physical adsorption such as charge-charge interactions, hydrophobic interactions, or hydrophilic interactions. Labeling compounds include, but are not limited to, compounds or derivatives of rhodamine, fluorescein, coumarin, orange B, crystal violets, toluidine blue, methyl violet, nuclear fast red, methylene blue, malachite green, magenta, acriflavine, and other azo compounds.

In another embodiment the surface modification, such as a zwitterionic polymer, is labeled by incorporating one or more reactive labeling monomers into the polymer backbone during polymerization. These labeling monomers include, but not limited to, FITC-methacrylate, FITC-acrylate, rhodamine-methacrylate, rhodamine-acrylate, their derivatives or any other fluorescent acrylate, methacrylate, acrylamide, vinyl compound, diol or diamine. Incorporation of these groups can allow for convenient measurement of conformality and/or coating thickness. This may be particularly useful as a quality control metric for conformality verification during manufacturing of the coating on an underlying device.

In another embodiment, the surface modification is stained with one or more compounds, which can be easily visualized under an electronic microscope (SEM or TEM). These compounds include, but not limited to osmium tetroxide and ruthenium tetroxide.

D. Bioactive Agents

Therapeutics, diagnostic, and/or prophylactic agents can be immobilized on a substrate. These agents can interact passively or actively with the surrounding in vivo environment. The agents can also be used to alter the surrounding in vivo chemistry or environment. Two or more agents can be immobilized to a substrate surface, wherein the activity of the two agents is greater than either of the agents alone. A substance, material or agent that is not considered active, can become active if an active agent is immobilized on the substance, material or agent. Active agents include, but are not limited to inorganic compounds, organometallic compounds, organic compounds or any synthetic or natural, chemical or biological compounds of known or unknown therapeutic effect.

Cell adhesion agents can be immobilized to the compositions described herein. The efficacy of a cell adhesion agent in binding cells in complex environments may be enhanced by reducing non-specific protein adsorption on the surface from which they are presented, given that cell attachment may be a competitive process with other protein adsorption. Further, there may an advantage to resisting attachment of any cells other than those specifically targeted by the cell adhesion agent to prevent competitive blocking of the surface.

Examples of desirable cell attachment agents include, but are not limited to, integrin binders. Exemplary integrin binders include, but are not limited to, RGD peptides, along with a number of variants that include RGD motifs. Longer variants of this peptide may have more specific target cell binding. Further, the ability to present locally dense concentrations of cell attachment agents may increase the effectiveness of cell attachment by creating multimeric interactions. Other cell adhesion agents include, but are not limited, to REDV peptides. Tailored integrin binders can be used for a variety of applications including osteointegration.

Cell adhesion agents that bind specific immune cells may also benefit from attachment to zwitterions. Adhesion of immune cells to the biomaterial surface activates these cells and prefaces their phenotypic response, such as the transition of monocytes to macrophages that can result, in some cases, in the fusion into undesirable foreign body giant cells. The inherent resistivity to random protein fouling that zwitterions possess provides a unique platform to couple biomolecules that act as specific ligands for immune cells including neutrophils and monocytes. Selection of appropriate ligands may prime these cells for beneficial instead of detrimental functions. These ligands include peptides or proteins that specifically bind immune cell receptors such as integrins, selectins, complement, or Fc gamma. When bound to these cell-associated proteins, such ligands may stimulate intracellular signaling pathways that lead to responses including cytoskeletal rearrangements, production and secretion of molecules including chemokines, cytokines and other chemoattractants, and induction of apoptosis. Desirable behaviors that could be tailored by presentation of biomolecules via zwitterionic tethers may include prevention/reduction in the secretion of proinflammatory cytokines, enhancement of phagocytosis, and modulation of the release of soluble factors that influence tissue-device integration.

Osteointegration may also be promoted or induced by factors which would benefit from the non-fouling properties and stable presentation of non-fouling materials, such as zwitterions. Osteointegration promoting agents include, but are not limited to, bone-morphogenic proteins, such as BMP2 and shortened analogues thereof. Non-fouling surfaces, such as zwitterionic surfaces, may enhance the activity of agents designed to promote desired cell regrowth over a surface. Reducing attachment of neutrophils and macrophages may inhibit the foreign body response and enable desired cell attachment and growth process to be favored.

Presentation of antithrombotic agents may also be more effective when tethered to non-fouling materials, such as zwitterionic materials, relative to other tethers. The process of thrombosis involves both surface and bulk pathways. Zwitterions have shown an ability to reduce platelet attachment and activation, reducing one pathway. Combining an active antithrombotic that assists in the reduction of platelet activation or directly targets additional pathways for thrombosis with a zwitterionic tether could enhance the antithrombotic effect compared to either a non-platelet adherent surface or the antithrombotic agent alone. Suitable antithrombotic agents include, but are not limited to, thrombomodulin, heparin, reversible albumin binders, tissue plasminogen activator binders, transglutimase, reversible NO binders, polylysine, sulphonated polymers, thrombin inhibitors including hirudin, urokinase, and streptokinase.

Device-centered infection remains a large problem. Non-fouling materials, such as zwitterions materials, can by themselves diminish microbial adhesion and retard biofilm development. Prevention of microbial adhesion and biofilm can be further enhanced on non-fouling surfaces, such as zwitterionic surfaces, by presentation of antimicrobials including, but not limited to, membrane-targeting antimicrobial agents, antimicrobial peptides and small molecule antimicrobial agents. Generally, antimicrobial peptides are cationic molecules with spatially separated hydrophobic and charged regions. Exemplary antimicrobial peptides include linear peptides that form an α-helical structure in membranes or peptides that form β-sheet structures, optionally stabilized with disulfide bridges in membranes. Representative antimicrobial peptides include, but are not limited to, cathelicidins, defensins, dermcidin, and more specifically magainin 2, protegrin, protegrin-1, melittin, 11-37, dermaseptin 01, cecropin, caerin, ovispirin, cecropin A melittin hybrid, and alamethicin, or hybrids or analogues of other AmPs. Naturally occurring antimicrobial peptides include peptides from vertebrates and non-vertebrates, including plants, humans, fungi, microbes, and insects.

Antimicrobial peptides can be made from naturally occurring amino acids, non-naturally occurring amino acids (e.g., synthetic or semisynthetic amino acids and peptidomimetics), or combinations thereof. Antimicrobial peptides which retain their activity when immobilized on a surface are generally referred to as membrane-targeting antimicrobial agents. Antimicrobial peptides can be immobilized on the non-fouling coating, the substrate, the undercoating or combinations thereof by reacting a functional group on the peptide with a functional group on the non-fouling coating, the substrate, and/or the primer coat. For example, the peptide can be designed to have a cysteine residue which can be used to immobilize the peptide on a surface by reacting the thiol group of the cysteine residue with a thiol-reactive group on the surface.

Tethering of these agents via non-fouling materials, such as zwitterions, should provide stable, long-term activity. Additionally, immobilization of enzymes that degrade bacterial attachment and biofilm proteins, such as glycosylases, lyases, and serine-proteases, or those that degrade microbial communication signal molecules, such as N-acyl-homoserine lactone acylases, could provide improved efficacy in prevention of initial microbial adhesion events and subsequent biofilm formation.

Non-fouling surfaces, such as zwitterionic surfaces, may also present a particularly attractive surface for immobilization of biomolecules, such as antibodies, for use as biosensors. Immobilized antibodies on non-fouling surface surfaces, such as zwitterionic surfaces, have been demonstrated to retain both antibody activity and antigen specificity in whole blood. "Smart" implanted medical devices that detect undesirable activation of specific immune pathways, such as proinflammatory cytokines, or the presence of a possible infectious agent, perhaps through detection of a secreted microbial toxin, could be designed, for example, by utilizing specific antibodies or biomolecules tailored to monitor these threats. Appropriate therapeutic strategies could then be employed before an unfavorable outcome, such as infection, arises. The stability of the zwitterionic molecule in vivo provides a unique advantage in this type of scenario due to its longevity.

III. Methods of Making Coated Substrates

Non-fouling coatings created using graft-from methods may be highly resistant to fouling by protein, bacteria, or other agents. Methods of making these coated substrates are described below.

A. Undercoating or Precoating

Medical device substrates are often composed of multiple different materials, each with its own surface properties. Even devices composed primarily of a single polymer may be made up of material blends and can include plasticizers, radio-opacity agents, and other additives all of which will affect substrate surface properties. In order to insure uniform surface composition for maximizing coating adhesion and efficacy, a precoat of a single polymer or polymer blend may be placed over the substrate. In a particular embodiment, the undercoating coat contains a single polymer. The polymer can be deposited on the substrate using a variety of techniques known in the art, such as solvent casting or dipping, optionally covalent crosslinking the undercoating coat once it has been applied to the substrate. Use of a single polymer undercoating layer, for example, can result in the formation of a coating surface that has a uniform identity and concentration of functional groups.

The undercoating layer may contain a radiopaque agent, such as $BaSO_4$ or bismuth, to aid in radiographic imaging of the substrate. In one embodiment the polymer is Tecoflex-93A or Carbothane 85A, optionally containing 0 to 40% by weight $BaSO_4$.

The undercoating layer can also include, but is not limited to, polymers such as polystyrene and substituted polystyrenes, polyethylene, polypropylene, poly(urethane)s, polyacrylates and polymethacrylates, polyacrylamides and polymethacrylamides, polyesters, polysiloxanes, polyethers, poly(orthoester), poly(carbonates), poly(hydroxyalkanoate)s, polyfluorocarbons, PEEK, Teflon, silicones, epoxy resins, KEVLAR®, NOMEX®, DACRON®, nylon, polyalkenes, phenolic resins, PTFE, natural and synthetic elastomers, adhesives and sealants, polyolefins, polysulfones, polyacrylonitrile, biopolymers such as polysaccharides and natural latex copolymers thereof, and combinations thereof.

In another embodiment, the undercoating layer contains small molecules or functional groups including, but not limited to, hydroxyl groups, amino groups, carboxylic groups, azide groups, azo groups, alkyl groups, alkene groups, alkyne groups, and siloxane groups. These functional groups can be used as anchoring point from which to graft the non-fouling material and/or to attach therapeutic, diagnostic, or prophylactic agents.

Coating titanium substrates with a high density of non-fouling coatings may include surface modification to introduce functional groups on the titanium surface to covalently attach the coating. For example, hydroxyl groups can be created on the substrate surface using an oxidative piranha solution. These groups can then be used to covalently bind anchoring molecules presenting organic functional moieties. Alternatively a titanium oxide layer can be grown on the surface of titanium by heating in air at very high temperatures, e.g., 773-1073° K prior to piranha treatment.

Functional groups for anchoring undercoatings to titanium include, but are not limited to, silane, phosphonic acid, and catechol groups. For example, trimethoxy silanes and trichloro silanes can be introduced on to the surface of titanium substrates by exposing the substrate to a solution of the silane. The functional groups can be in the form of small molecules, oligomers, and/or polymers, including copolymers.

The precoated substrate can then be further functionalized using the coating methods described below.

B. Graft From Coating Methods

The compositions described herein are generally prepared using graft from methods. The non-fouling material can be grafted directly from the substrate surface by growing the polymer from a reactive functional group on the substrate surface. Alternatively, the substrate can be coated with an undercoating layer from which the polymer is grown.

Graft from coating methods may produce robust and dense non-fouling coatings, grown directly on the substrate surface. Much higher coating densities can be obtained using this method relative to graft to coatings because small initiator molecules can be packed closer together on and/or in the substrate and/or undercoating surface, where polymerization is initiated and propagated, than larger polymer molecules synthesized in solution. Preferably, for the manufacture of medical devices, the chemistry utilized must be robust and able to overcome small surface defects. Chemistries requiring the formation of self assembled monolayers (SAMs) or other single molecular initiator layers are less likely to result in manufacturable coatings. For some applications, processes that do not require strict control of reaction conditions (absence of oxygen, anhydrous solvents, etc.) may be preferable.

Monomers can be designed such that their reactivity ratios give alternating copolymers, periodic copolymers with a pre-specified ratio of each monomer, random copolymers or homopolymers. Inclusion of more than two reactive groups on each monomer unit allows for the formation of star polymers, dendrimers, regularly branched polymers, randomly branched polymers, and brush polymers.

Polymer brushes, combs, linear and branched copolymers, dendrimers, tethers and hydrogels can be formed by known synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical polymerization. In a preferred embodiment, the polymer is formed using a redox polymerization process.

1. Non-Radical Processes

The graft from polymerization can propagate through a cationic or anionic reaction, where the substrate surface acts as the cation or anion initiator or a cationic or anionic initiator is immobilized on the substrate and the monomer contains a reactive olefin. Examples of anionic polymerization are anionic ring opening, as in the case of synthesizing polycaprolactone or polycaprolactam, where the polymerization proceeds through a lactone or lactam moiety in a ring structure containing a pendant zwitterion group. Alternatively, an organic ring containing one or more units of unsaturation and a pendant zwitterionic group are polymerized. In one embodiment a pendant olefin is included in the monomer unit and is used for crosslinking, such as in ring opening metathesis polymerization (ROMP).

Functional groups through which graft from polymerizations can proceed can be introduced in a variety of ways. For example, silicone polymers can also be treated with triflic acid to introduce SiH groups which can be subsequently utilized to attach silicone chains containing appropriate functional groups to the surface. Polyurethane substrates can be treated using a plasma treatment with $CO_2$, $O_2$, and ammonia. The resulting hydroxyl and/or amine groups can be acrylated to form vinyl moieties on the surface followed by tethering of the polymer brushes. Alternately, amine functionalities can be introduced on the surface of a polyurethane substrate by treatment with a di-amino molecule such as hexamethyldiamine through aminolysis. Semi- and fully interpenetrating polymer networks can be used to introduce a polymer with amino groups into a polyurethane substrate.

In another embodiment, polymerization is initiated by functionalizing the surface of the substrate with a small molecule, such as an azide or terminal alkyne, and exposing the substrate to alternating reactions between one or more different monomers each containing two or more reactive sites of a single type. For example a monomer containing two azide functional groups is reacted with the substrate surface followed by reaction with a monomer containing two terminal alkynes.

2. Radical Processes

In one embodiment, the non-fouling polymeric materials are grafted from the substrate using a radical polymerization process. The polymerization conditions described herein are generally mild compared to other methods of polymerization and thus do not significantly alter the mechanical properties, flexibility, or dimensional properties of the underlying substrate.

Examples of radical polymerization processes include, but are not limited to, UV, thermal, and redox initiated processes. In particular embodiments, a coating is grown directly from the substrate surface, by first absorbing or adsorbing one or more initiators, such as an ultraviolet (UV), thermal, or redox initiator into or onto the surface of the substrate and initiating polymerization of one or more monomers from the surface. Polymerization is typically initiated by exposing the initiator-imbibed substrate with a solution or suspension of the monomer or monomers to be polymerized.

Chain transfer agents can be added to the monomer solution to mediate the graft from radical polymerization reaction kinetics. Chain transfer agents include, but are not limited to, molecules containing halocarbons, thiols, dithiocarbamates, trithiocarbonates, dithioesters, xanthates. Examples of chain transfer agents are bromotrichloromethane and 4-methylbenzenethiol. In one embodiment the radical polymerization graftings are mediated using 2,2,6,6-tetramethylpiperidine-1-oxyl (TEMPO). In one embodiment the radical polymerization graftings are mediated using reversible addition fragmentation transfer (RAFT) agents.

For those graft from methods that require an initiator, the initiator can be introduced to the substrate surface using a variety of methods. In one embodiment, the initiator is introduced into and/or onto the substrate's surface by physio-adsorption, wherein the initiator is dissolved in a solvent or combination of solvents. The substrate is submerged for a pre-determined amount of time in a solvent or solvent combination containing the initiator. The substrate and/or undercoating layer is allowed to swell ultimately imbibing initiator into the substrate bulk on or near the substrate's surface. The quantity of initiator introduced to the substrate can be controlled by changing the concentration of the initiator in the solvent solution and/or by changing the amount of time the substrate is allowed to soak in the initiator solution.

In another embodiment the initiator is introduced to the substrate surface or undercoating layer by chemi-adsorption. In this embodiment, the initiator contains a reactive group that will chemically react with the substrate surface forming a chemical bond between the substrate and the initiator.

In still another embodiment the initiator is introduced to the substrate surface by co-deposition of the initiator molecule with another material. For example the initiator can be dissolved in a polymer solution. A thin film of polymer and initiator are deposited onto the substrate by dipping the substrate in this solution. The initiator can either directly or indirectly initiate polymerization on the surface of the substrate, or initiate polymerization on the co-deposition material. Examples of co-deposition materials include, but are not limited to, Tecoflex, CARBOTHANE®, PELLATHANE®, polyurethanes, polystyrenes, polyesters or sol-gels.

In yet another embodiment the initiator is directly incorporated into the backbone of a coating material, such as brominated polyurethane. In this embodiment the coating is directly applied to the substrate surface and polymerization reactions are initiated directly from the applied coating.

For non-fouling surfaces, increasing the concentration of initiator through imbibing or an undercoating can increase chain graft density. Having a higher chain graft density allows the non-fouling polymer to better prevent the penetration of fouling agents into the coating by increasing the number of non-fouling groups and/or increasing the number of decreasing the inter-polymer chain distance to decrease the penetration of fouling molecules into the coating. In one embodiment, the initiator is imbibed (absorbed) into and onto the surface of the substrate. For example, the substrate can be exposed to a solution of the initiator in an organic solvent. The solvent can cause the substrate to swell, allowing the initiator to absorb into the substrate. The degree of absorption into the substrate is a function of the amount and the duration of the swelling of the substrate.

As discussed above, oxygen can act as an inhibitor in free radical polymerization as it can react quickly with the free radicals generated by the initiator to form stable radical species, which in turn can react with other radical species to form unreactive species which terminate the polymerization. Therefore, creating an oxygen-free environment by degassing with nitrogen or argon or vacuum is typically used to remove oxygen before and during polymerization. However, it would preferable not to require such degassing steps in commercial production.

Alternatively, oxygen in the system can be minimized by filling the reactor with the reaction mixtures thus physically displacing the oxygen in the reactor. In another embodiment, reagents which scavenge oxygen can be added to the reaction mixture. Suitable oxygen-scavenging reagents include, but are not limited to, sodium (meta) periodate, riboflavin, and ascorbic acid. These agents may improve the efficacy of the resulting polymer if the polymerization is done under conditions that are not inert.

i. UV Initiators

In one embodiment, the initiator is an ultraviolet (UV) initiator. The substrate and initiator are typically placed into an aqueous, degassed, solution containing a zwitterionic monomer and exposed to UV light, initiating the graft from radical polymerization on the substrate surface.

Examples of UV radical initiators include, but are not limited to, 1-Hydroxycyclohexyl phenyl ketone, 2,2-Diethoxyacetophenone, 2-Benzyl-2-(dimethylamino)-4'-morpholinobutyrophenone, 2-Hydroxy-2-methylpropiophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 4,4'-Dimethylbenzil, Benzoin ethyl ether, Benzoin isobutyl ether, Benzoin methyl ether, Benzoin, 2-Methylbenzophenone, 3,4-Dimethylbenzophenone, 3-Hydroxybenzophenone, 3-Methylbenzophenone, 4,4'-Bis(diethylamino)benzophenone, 4,4'-Dihydroxybenzophenone, 4,4'-Bis[2-(1-propenyl)phenoxy]benzophenone, 4-(Diethylamino)benzophenone, 4-Benzoylbiphenyl, 4-Hydroxybenzophenone, 4-Methylbenzophenone, Benzophenone-3,3',4,4'-tetracarboxylic dianhydride, Benzophenone, Methyl benzoylformate, Michler's ketone, Sulfoniums, iodiums, 2-(4-Methoxystyryl)-4,6-bis(trichloromethyl)-1,3,5-triazine, Diphenyliodonium p-toluenesulfonate, N-Hydroxy-5-norbornene-2,3-dicarboximide perfluoro-1-butanesulfonate, N-Hydroxynaphthalimide triflate, 2-tert-Butylanthraquinone, 9,10-Phenanthrenequinone, Anthraquinone-2-sulfonic acid sodium salt monohydrate, Camphorquinone, Diphenyl (2,4,6-trimethylbenzoyl)phosphine oxide, 10-Methylphenothiazine, thioxanthones, and IRGACURE 2959.

ii. Thermal Initiators

In another embodiment a heat activated (thermal) initiator is used, in place of the UV initiator described above, and the graft from polymerization is initiated by heating the aqueous monomer solution temperature to a desired temperature and holding the temperature constant until the polymerization is complete.

Suitable thermal initiators include, but are not limited to, tert-Amyl peroxybenzoate, 4,4-Azobis(4-cyanovaleric acid), 2,2'-Azobis[(2-carboxyethyl)-2-methylpropionamidine], 2,2'-Azobis(4-methoxy-2,3,-dimethylvaleronitrile), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate, Cumene hydroperoxide, Cyclohexanone peroxide, Dicumyl peroxide, Lauroyl peroxide, 2,4-Pentanedione peroxide, Peracetic acid, Potassium persulfate.

The temperature to which the solution is heated is dependent on the monomer and/or the initiator. Examples of thermal radical initiators include, but are not limited to, azo-compounds such as azobisisobutyronitrile (AIBN) and 1,1'-Azobis(cyclohexanecarbonitrile) (ABCN). The graft from radical polymerization reaction is quenched by rapidly cooling the reaction solution in liquid nitrogen.

iii. Redox Initiators

In another embodiment, a redox initiator system is used to initiate polymerization from the surface of the substrate. The redox initiator system typically includes a pair of initiators: an oxidant and a reducing agent. The redox chemistry described herein can be modified to prepare non-fouling polymeric materials, for example, in the form of brushes, such as zwitterionic polymer brushes. Redox initiation is regarded as the most effective one-electron transfer reaction to effectively generate free radicals under mild conditions.

Suitable oxidants include, but are not limited to, peroxide, persulfates peroxydisulfates, peroxydiphosphate, permanganate, salts of metals such as Mn(III), Ce(IV), V(V), Co(III), Cr(VI) and Fe(III).

Suitable reducing agents include, but are not limited to, metal salts such as Fe(II), Cr(II), V(II), Ti(III), Cu(II), Ag(I), and oxyacids of sulfur, hydroxyacids, alcohols, thiols, ketones, aldehydes, amine, and amides.

Polymerization can be initiated by radicals formed directly from the redox reaction and/or by macroradicals formed by the abstraction of a hydrogen atom from the substrate by the transient radicals formed during the redox reaction.

In one embodiment, the substrate is coated with a undercoating coating and the non-fouling material is grafted from the undercoating layer by redox polymerization. The undercoating coating contains oxidants or reducing agents. In a preferred embodiment, the undercoating layer contains one or more reducing agents, such as acids, alcohol, thiols, ketones, aldehydes, amines and amides. An oxidant is used to react with one or more functional groups of the undercoating layer to form radicals which initiate the graft from polymerization.

In a particular embodiment, the undercoating layer is a copolymer with pendant groups of aliphatic chains containing silanol and/or hydroxyl groups. Such materials can be used to form a undercoating layer on polymeric substrates, such as polyurethane (PU). An oxidant, such as an oxidate of Ce(IV), reacts with the hydroxyl group under mild conditions to form hydroxyl radicals in the undercoating layer to grow the zwitterionic polymer brushes.

In still another embodiment, a pair of peroxides and metal salts (such as Fe(II) as used in the Fenton Reaction) is used in the redox polymerization to build the zwitterionic polymer brushes on polymers such as polyurethane. Peroxides such as benzoyl peroxide, lauroyl peroxide, hydrogen peroxide, or dicumyl peroxide are imbibed into the polymer such as polyurethane by dipping the polymer into a peroxide solution in an organic solvent for a predetermined period of time and dried. The peroxide containing polymer is put into a solution of monomer. The redox polymerization is initiated by the addition of metal ions, for example metal ions of Fe(II), such as Fe(II) chloride, Fe(II) sulfate, ammonium Fe(II) sulfate, or Fe(II) gluconate at room temperature or elevated temperature to the monomer solution.

For modifying the surface of an article and/or surface graft polymerization, it has been found particularly useful to use hydrophobic-hydrophilic redox pairs. For example, a hydrophobic material can be imbibed with the hydrophobic part of a redox initiating system. "Imbibing" may include physically adsorbing the initiator onto the surface and/or the initiator partially penetrating the hydrophobic surface. Imbibing can be aided by use of a solvent.

The imbibed surface is next modified by treatment with hydrophilic monomers in the presence of the hydrophilic member of the redox pair. The grafting may be initiated at the hydrophobic-hydrophilic interface by redox processes. This method may be useful for coating polymer surfaces having complicated geometrical shapes.

The use of hydrophobic-hydrophilic pairs has many advantages including limiting diffusion of the redox initiators into the grafting aqueous and the substrate due to the hydrophobic and hydrophilic nature of the initiators. Uncontrolled diffusion of the redox partners can lead to solution polymerization and less surface functionalization. For example, if both partners are hydrophilic, polymerization is more likely to occur in the monomer solution, decreasing the amount of polymer grafted from the substrate. Uncontrolled diffusion of the redox partners can also lead to unwanted reactions from radicals in the substrate.

Suitable initiator partners include, but are not limited to, tert-Amyl peroxybenzoate, 4,4-Azobis(4-cyanovaleric acid), 1,1'-Azobis(cyclohexanecarbonitrile), 2,2'-Azobisisobutyronitrile (AIBN), Benzoyl peroxide, 2,2-Bis(tert-butylperoxy)butane, 1,1-Bis(tert-butylperoxy)cyclohexane, 2,5-Bis(tert-butylperoxy)-2,5-dimethylhexane, 2,5-Bis(tert-Butylperoxy)-2,5-dimethyl-3-hexyne, Bis(1-(tert-butylperoxy)-1-methylethyl)benzene, 1,1-Bis(tert-butylperoxy)-3,3,5-trimethylcyclohexane, tert-Butyl hydroperoxide, tert-Butyl peracetate, tert-Butyl peroxide, tert-Butyl peroxybenzoate, tert-Butylperoxy isopropyl carbonate Cumene hydroperoxide, Cyclohexanone peroxide, Dicumyl peroxide, Lauroyl peroxide, 2,4-Pentanedione peroxide 125, Peracetic acid, and Potassium persulfate.

Other suitable redox systems include, but are not limited to, (1) Peroxides in combination with a reducing agent such as hydrogen peroxide or alkyl, aryl, or acyl peroxides in combination with $Fe^{2+}$, Cr2+, V2+, Ti3+, Co2+, Cu+, or amines; transition metal ion complexes, e.g., copper (II) acetylacetonate and peroxides; zinc chloride and AIBN; (2) inorganic reductants and inorganic oxidants, such as —$O_3SOOSO_3$, $HSO_3^-$, $SO_3^{2-}$, $S_2O_3^{2-}$, $S_2O_5^{2-}$ in combination with an inorganic oxidant such as $Fe^{2+}$, $Ag^+$, $Fe^{3+}$, $ClO^{3-}$, $H_2O_2$; (3) organic-inorganic redox pairs, such as oxidation of an alcohol by $Ce^{4+}$, $V^{5+}$, $Cr^{6+}$, $Mn^{3+}$; (4) monomers which can act as a component of the redox pair, such as thiosulfate plus acrylamide, thiosulfate plus methacrylic acid, and N,N-dimethylaniline plus methyl methacrylate, and (5) boronalkyl-oxygen systems.

For substrates requiring coating on both internal and external surfaces, additional considerations are required for initiating polymerization. Thermal initiators can be used; however, the elevated temperature typically required can adversely affect the substrate material. UV based approaches must be designed such that they can penetrate through the material or can be applied intralumenally, for instance from a fiber optic source threaded into the lumen. This may be achieved by selecting a photoactive initiator which is labile at a UV wavelength not absorbed by the substrate polymer. Generally, lower wavelength UV irradiation is less absorbed and penetrates more readily than higher wavelength UV.

In contrast, redox chemistries generally do not require a direct line of sight to a light source to initiate polymerization since polymerization is not initiated photolytically and therefore may be advantageous for coating substrates that have one or more surfaces that are difficult to expose to the UV source, such as catheter lumens. Further, redox polymerization typically can be done at low temperatures, for example less than 60° C., less than 55° C., less than 50° C., less than 45° C., less than 40° C., less than 35° C., or less than 30° C.

Non-fouling polymeric materials can be grafted from a surface using the general procedures described in the examples. In one embodiment, a solution containing 1% to 5% (wt/wt) urethane can be prepared by dissolving the appropriate weight of urethane pellets in a suitable organic solvent, such as tetrahydrofuran, and diluting the solution with a second solvent, such as methanol. The final methanol concentration is preferably between 10%-90%, more preferably between 15%-85%, most preferably 60%. One or more suitable initiator molecules, such as benzoyl peroxide or dicumyl peroxide, are added to the polymer solution at a concentration typically from about 0.25% to about 10%. However, concentrations below 0.25% and above 10% can be used.

Any desired substrate can be exposed to the polymer/initiator solution once or multiple times until a desired coating thickness and/or initiator surface concentration has been achieved. The solvent is typically removed, for example by evaporation, from the coated substrate between each exposure to the solution, in a case where the substrate is exposed multiple times. After the final exposure, the substrate is allowed to sit for at least 10 minutes to allow any residual solvent to evaporate, prior to placing in a polymerization reaction mixture.

The process described above can be used to imbibe high concentrations of the initiator into and/or onto the substrate or undercoating layer. High initiator concentrations result in highly densely coated surfaces which improves the non-fouling activity of the composition. For example, highly densely coated surfaces contain polymer chains having inter-polymer chain distances sufficiently small to prohibit penetration of fouling molecules into the coating thus fouling the substrate surface.

The general procedure described above can be modified as necessary to accommodate different substrate materials, initiators systems, and/or monomer compositions.

C. Immobilization of Bioactive Agents on the Substrate

In a graft from method, the active agent will typically be immobilized on the non-fouling material after the non-fouling material has been grown from the surface.

The active agent can be co-immobilized with the non-fouling material in a side by side structure. In the graft from methods, a tether can be grown from the surface and the active agent immobilized on the tether. Alternatively, the active agent can be immobilized directly on the surface without the use of a tether.

The active agents can be immobilized covalently or non-covalently directly on the substrate, on the undercoating layer, on the non-fouling material, or combinations thereof. In one embodiment, the active agent is immobilized covalently by reacting one or more functional groups on the active agent with one or more functional groups on the substrate, undercoating layer, and/or non-fouling material. Covalent bonds can be formed by a variety of reaction mechanisms including, but not limited to, substitution, addition, and condensation reactions.

IV. Methods of Use

The materials described above may be in the form of a medical device to which the non-fouling material is applied as a coating. Suitable devices include, but are not limited to, surgical, medical or dental instruments, ophthalmic devices, wound treatments (bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, especially human tissue.

A. Fibrous and Particulate Materials

In one embodiment, the non-fouling materials are coated directly on a fibrous material, incorporated into a fibrous material or coated indirectly on a fibrous material (e.g. coated on a different surface coating). These include wound dressings, bandages, gauze, tape, pads, sponges, including woven and non-woven sponges and those designed specifically for dental or ophthalmic surgeries (See, e.g., U.S. Pat. Nos. 4,098,728; 4,211,227; 4,636,208; 5,180,375; and 6,711,879), paper or polymeric materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimize or eliminate contamination of the cultures, while allowing selective attachment of the desired cells through the incorporation of directed adhesion proteins into the material.

The non-fouling agents are also readily bound to particles, including nanoparticles, microparticles, millimeter beads, or formed into micelles, that have uses in a variety of applications including cell culture, as mentioned above, and drug delivery. Non-fouling, biocompatible, polymeric micelles would prevent protein denaturation preventing activation of the immune response allowing for a more stealthy delivery of the desired therapeutic.

B. Implanted and Inserted Materials

The non-fouling material can also be applied directly to, or incorporated in, polymeric, metallic, or ceramic substrates. Suitable devices include, but are not limited to surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal, interventional, etc.), shunts, wound drains, dialysis membranes, infusion ports, cochlear implants, endotracheal tubes, guide wires, fluid collection bags, sensors, wound treatments (dressings, bandages, sutures, cell scaffolds, bone cements, particles), ophthalmic devices, orthopedic devices (hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these. Preferably, the non-fouling coating herein does not significantly adversely affect the desired physical properties of the device including, but not limited to, flexibility, durability, kink resistance, abrasion resistance, thermal and electrical conductivity, tensile strength, hardness, burst pressure, etc.

In one embodiment, the substrate is a vascularly inserted catheter such as a peripherally inserted central catheter (PICC), central venous catheter (CVC) or hemodialysis catheter, venous valves, punctual plugs, and intra-ocular devices and implants.

In another embodiment, the substrate is a vascularly inserted catheter formed from a medical grade polyurtheth-ane or CARBOTHANE® or formed from a material coated with a medical grade polyurethane or polycarbothane.

C. Coatings, Paints, Dips, Sprays

The non-fouling materials can also be added to paints and other coatings and filters to prevent mildew, bacterial contamination, and in other applications where it is desirable to prevent fouling, such as marine applications (ship hull coatings), contact lenses, dental implants, coatings for in vivo sensors, devices for separations, such as membranes for microbial suspension, biomolecule separation, protein fractionation, cell separation, waste water treatment, bioreactors, and food processing.

Other applications include the treatment of fibers, particulates and films for applications in textiles, additives, electric/optical appliances, packaging materials and colorants/inks.

EXAMPLES

Example 1. Grafting Zwitterionic Polymer onto Polyurethane Using Benzophenone UV Initiator Step 1. Benzophenone Soak. Polyurethane samples were placed in a 1 L VWR or Pyrex bottle. To this bottle was added 160 mL of a 10% (w/v) solution of benzophenone in acetone. After adding a stir bar, the bottle was capped, covered with aluminum foil to protect from light, and stirred overnight. The solution of benzophenone was decanted from the polyurethane pieces; 150 mL acetone was added, and stirred with the polyurethane samples for 30 minutes, covered with aluminum foil. The samples were filtered using a large Buchner funnel and rinsed with acetone. The samples were placed into a glass Petri dish, dried with a stream of nitrogen gas, and placed on aluminum foil in the dark overnight.

Step 2. UV Grafting. The bottom of quartz glass tubes were stoppered with rubber septa and secured with parafilm. Teflon tape was wrapped across the top of the tube to ensure a tighter seal with the top stopper. The benzophenone-soaked polyurethane samples were placed in the tubes, and the top of the tube was stoppered with rubber septa and secured with parafilm. After purging the 10% (w/v) SBMA solution in water and all of the quartz reaction tubes with argon for 35 min, the monomer solution was transferred to each reaction tube, and the ends secured with parafilm. Any bubbles were tapped so that they settled above the solution. The tubes were placed upright in a UV-reactor and irradiated with spinning for 6 hours. After removing the tubes from the reactor, each polyurethane sample was rinsed each with hot water and shaken overnight in 1×PBS and stored in plastic culture tubes in 1×PBS at 4° C. An analogous method may be used to create carboxybetaine coatings using monomers such as CBMA instead of SBMA.

Each of the SBMA samples produced on 10 French polyurethane rods were assessed for anti-thrombotic performance by exposing them to freshly harvested bovine blood in a flow loop for 2 hours with radiolabeled platelets. Both SBMA and CBMA samples prepared with this UV method showed approximately an 80% reduction in adsorbed platelets and substantial visual reduction of thrombus.

Example 2: Graft of Zwitterionic Polymer onto Polyurethane with Undercoating and Ce(IV) Redox Polymerization Synthesis of Copolymer 50 mL of anhydrous methanol is added into a 250 mL dry flask together with 4 mL of lauryl methacrylate and 4 mL of 2-hydroxyethyl methacrylate. After purging with nitrogen for 5 min, 0.3 mL of 3-(trimethoxysilyl)propyl methacrylate is added to continue the degassing. The polymerization is started with the addition of 0.2 g of azobisisobutyronitrile (AIBN) at 60° C. under inert atmosphere with stirring for 18 h. The reaction mixture is purified by dialysis against anhydrous methanol (molecular weight cutoff 2,000) for h to get the copolymer solution (undercoating solution).

Undercoating Coating

Polyurethane substrates, for example of 10 French polyurethane rods, are dipped into 0.5% of solution of undercoating in methanol for 3 min at ambient condition, and taken out and dried at 60° C. for 1 h. The above dipping and dry procedure is repeated 4 times before the samples are dried at 60° C. for 18 h. Then they are washed with 1×PBS for 18 h before washing with DI water and dried by air.

Ce(IV) Mediated Graft Polymerization

The undercoating coated samples are added into the flask with 10% of SBMA aqueous solution with 1 mg/mL of ammonium cerium (IV) sulfate and purged with nitrogen for 15 min. Then the reaction is performed at 45° C. for 2 h under stirring. The samples are taken out and washed with PBS to remove the adsorbed homopolymer. By ELISA, the treated samples exhibit 83% of reduced fibrinogen adsorption.

Example 3: Graft of Zwitterionic Polymer onto Polyurethane with Dicumyl Peroxide-Fe(II) Gluconate Redox Polymerization Dicumyl Peroxide Imbibe 10 French polyurethane rods are soaked in 10% solution of dicumyl peroxide in acetone or methanol for 2 h, dried with air flow and kept in air for 18 h.

Redox Polymerization 10.5% of SBMA aqueous solution and dicumyl peroxide treated polyurethane rods are put into a flask with magnetic stir, and then purged with argon for 10 min before the addition of 100 mM of Fe(II) gluconate solution. The final solution of SBMA and Fe(II) gluconate are 10% (wt/wt) and 5 mM respectively. The purging with argon is continued for another 20 mins. Then the reaction is run at 60° C. for five hours. Then the samples are taken out and washed in 1×PBS overnight. By ELISA, the treated samples exhibit as high as 90% of reduced fibrinogen adsorption.

In order to evaluate the non-fouling activity of substrates having lumen, 14 French polyurethane double d lumen tubes were coated according to example 3. The treated samples exhibit as high as 90% reduced fibrinogen adsorption using the assay described above.

Example 4. Protein Adsorption and Biofilm Formation of Redox and UV SBMA-Coated Polyurethane Rods 24 Hour Colonization Assay Redox SBMA prepared in example 3, UV SBMA prepared in example 1, and control Carbothane rods were incubated with 50% Fetal Bovine Serum for 18 hours. Samples were then incubated with $S.$ $aureus$ ATCC 25923 for 24 hrs with a starting planktonic concentration of 1-3× $10^5$ CFU/mL in 1% TSB with agitation at 37° C. After 24 hrs, accumulated biofilm on materials was removed by sonication, and the total number of bacterial cells quantified through dilution plating. Further planktonic concentrations at the end of assay were monitored to ensure that there are not toxic leachable compounds that may create assay artifacts. After incubating the plates for 24 hr incubation at 37° C., colonies were counted and the number of viable cells that were present on each sample was determined. Each experiment was performed in triplicate using four samples of each material.

Relative to control, Redox SBMA samples demonstrated an average of 1.96 log(SD 0.57 log, p<0.001) reduction in colonization (n=44), and UV SBMA demonstrated an average of 2.34 log(SD 0.22 log, p<0.001) reduction (n=24).

Example 5. Anti-Thrombotic Activity of Carboxybetaine-Coated Rods

In Vivo Thrombosis Model

The extended in vivo performance of UV based carboxybetaine modifications prepared as described in Example 1 was demonstrated in a 7-day cephalic vein implantation of coated Tecoflex rods in sheep. Briefly, test articles consisting of 4 Fr.×15 cm Tecoflex® rods treated with CB modification or unmodified were inserted into the cephalic veins of the two year old male Suffolk sheep. After 7 days, the sheep were anesthetized, peripheral blood samples were drawn, and the cephalic veins were ligated and excised, leaving the implanted article in the vein during the removal process. The vein was then cut axially and carefully opened without disturbing thrombus on the implanted rods. The total thrombus mass on the coated and uncoated articles was assessed. Each animal received one coated and uncoated device to control for animal to animal variability. A 72% reduction in thrombus weight was seen relative to Tecoflex controls placed in the opposite veins of the same animals (see FIG. 1) and this reduction was clearly seen visually. These data show the ability of a non-adherent coating to prevent thrombosis formation and the potential for such coatings to retain activity for extended periods of time.

Example 6. Zwitterionic Homopolymer on Polyurethane with Dicumyl Peroxide Redox Polymerization Teeoflex SG-93A (2.5 g) was dissolved in refluxing tetrahydrofuran with vigorous stirring. The solution was cooled to room temperature and diluted with methanol. The final solution concentrations were 1% Tecoflex SG-93A, 40% Tetrahydrofuran, and 60% methanol. Dicumyl peroxide (2.5 g) was added to an aliquot of this polymer solution (25 g) and the mixture was stirred until all of the dicumyl peroxide dissolved.

Carbothane extrusions (14 french, 11 cm long, double D) were dipped in the initiator-polymer solution. Samples were dipped 1, 2, 4, or 8 times. Between each dip, the solvent was allowed to evaporate off of the substrate for 1 minute. After the final dip, all of the samples were allowed to rest at room temperature for 3 hours to remove any residual solvent. After solvent evaporation, 0.5 cm was cut from each end of the samples and the samples were then cut in half. The 5.0 cm samples were placed into 40 mL amber glass vials, which were sealed with septa.

Separate solutions of SBMA (91.2 g in 432 mL of deionized water) and Fe (II) Gluconate (1.02 g in 12 mL of deionized water) were deoxygenated by bubbling argon through each solution for 30 minutes with stirring. While these solutions were being deoxygenated, the amber glass vials containing 5 cm extrusions were flushed with argon for 30 minutes.

SBMA solution (36 mL) was added to each flask by syringe followed by addition of Fe(II) Gluconate solution (1 ml) by syringe. The vials were heated to 37° C. on an Anthill reaction shaker and the reaction was allowed to continue for 24 hours while shaking at 680 RPM.

After the reaction, all samples were removed from the reaction vials, rinsed three times with 1× phosphate buffered saline (PBS). The rinsed samples were soaked for 2 days in 1×PBS prior to assaying using a radio labeled fibrinogen assay.

We claim:

1. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the substrate is selected from the group consisting of metallic materials, wherein the metallic materials is selected from the group consisting of titanium and alloys thereof, stainless steel, tantalum, palladium, zirconium, niobium, molybdenum, nickel-chrome, cobalt or alloys thereof, and combinations thereof.

2. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the substrate is selected from the group consisting of ceramics, wherein the ceramic is selected from the group consisting of oxides, carbides, or nitrides of the transition metal elements or metalloid elements.

3. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the substrate is substantially thiol free.

4. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the non-fouling polymeric material is a zwitterionic polymer.

5. The method of claim 4 wherein the zwitterionic polymer is a homopolymer or copolymer comprising one more monomers having the following formula:

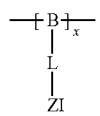

wherein B is selected from the group consisting of:

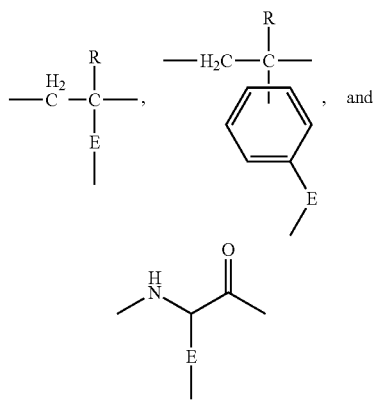

wherein R is selected from the group consisting of hydrogen, substituted alkyl, or unsubstituted alkyl;
E is selected from the group consisting of substituted alkyl, unsubstituted alkyl, —(CH$_2$)$_y$C(O)O—, and —(CH$_2$)$_y$C(O)NR$^2$—;
R$^2$ is selected from hydrogen and substituted or unsubstituted alkyl;
Y is an integer from 0-12;
L is absent or is a straight or branched alkyl group optionally including one or more oxygen atoms;
ZI is a zwitterionic group; and
X is an integer from 3 to 1000.

6. The method of claim 5, wherein ZI is selected from the group consisting of:

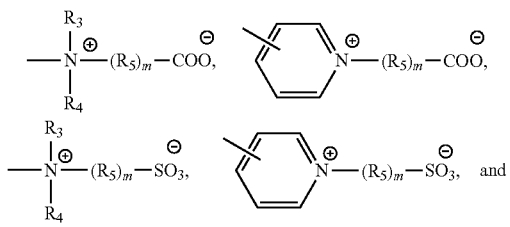

-continued

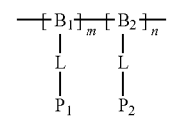

wherein
R$_3$ and R$_4$ are independently selected from the group consisting of hydrogen and substituted or unsubstituted alkyl;
R$_5$ is selected from the group consisting of substituted or unsubstituted alkyl, phenyl, and polyether groups; and
m is an integer from 1-7.

7. The method of claim 5 wherein x is from about 10 to about 500, from about 20 to about 250, or from about 30 to about 100.

8. The method of claim 5, wherein the zwitterionic polymer is a homopolymer of sulfobetaine methacrylate (SBMA) or sulfobetaine acrylamide.

9. The method of claim 5, wherein the zwitterionic polymer is a copolymer comprising sulfobetaine methacrylate (SBMA) or sulfobetaine acrylamide.

10. The method of claim 4, wherein the zwitterionic polymer has the following structure:

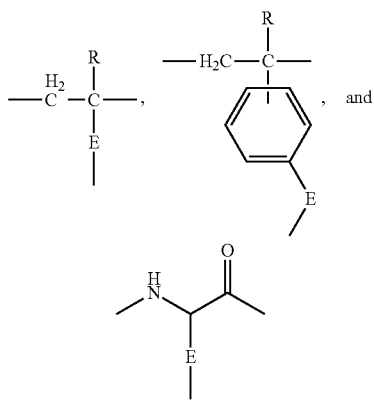

wherein
B$_1$ and B$_2$ are independently selected from the group consisting of:

R is selected from the group consisting of hydrogen, substituted alkyl, or unsubstituted alkyl;
E is selected from substituted or unsubstituted alkylene, —(CH$_2$)$_p$C(O)O—, and —(CH$_2$)$_p$C(O)NR$^2$—, wherein p is an integer from 0 to 12,
R$^2$ is selected from hydrogen and substituted or unsubstituted alkyl;
L is a straight or branched alkylene group optionally including one or more oxygen atoms;
P$_1$ is a positively charged group;
P$_2$ is a negative charged group;
m is an integer from 3 to 1000; and
n is an integer from 3 to 1000.

11. The method of claim 4, wherein the polymer comprises one or more monomers selected from the group consisting of:

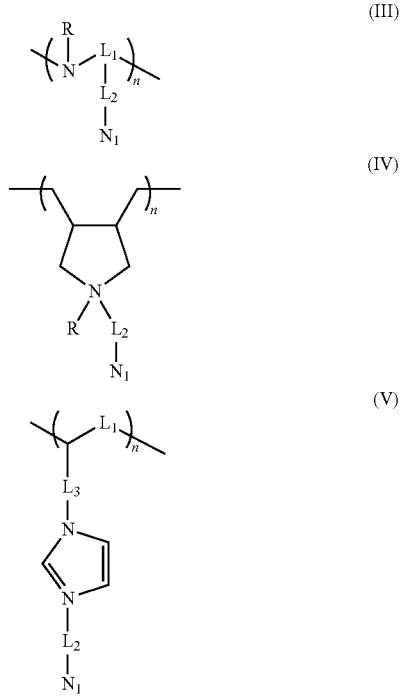

wherein
R is selected from and substituted or unsubstituted alkyl;
$L_1$, $L_2$, and $L_3$ are independently a straight or branched alkylene group optionally including one or more oxygen atoms; and
n is an integer from 3 to 1000; and
$N_1$ is a negatively charged group.

12. The method of claim 10, wherein the negatively charged group is selected from the group consisting of carboxylate group, —$SO_3^-$, —$OSO_3^-$, —$PO_3^-$, and —$OPO_3^-$.

13. The method of claim 10, wherein the positively charged group is a quaternized nitrogen or cationic phosphorous containing group.

14. The method of claim 10, wherein x, m, and n are from about 10 to about 500, from about 20 to about 250, or from about 30 to about 100.

15. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the non-fouling material is a non-zwitterionic polymer selected from the group consisting of polyethers, polysaccharides, polyvinylpyrrolidone, hydroxyethylmethacrylate, acrylonitrile-acrylamide copolymers, heparin, mixed charge polymers, and polymers containing hydrogen bond accepting groups.

16. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the polymeric material is formed by UV-initiated free radical polymerization.

17. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the polymeric material is formed by redox-initiated free radical polymerization, and wherein the non-fouling material is polymerized by radicals present in the substrate and/or undercoating layer, and further wherein the radicals are formed from a redox pair comprising a peroxide and a metal salt.

18. The method of claim 17, wherein the peroxide is imbibed in the substrate.

19. The method of claim 17, wherein the peroxide is dicumyl peroxide and the metal salt is Fe(II) gluconate.

20. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein one or more free radical initiators are imbibed into the substrate or the undercoating layer, wherein the one or more initiators is an ultraviolet (UV) initiator.

21. The method of claim 20, wherein the one or more free radical initiators are imbibed into the substrate, the undercoating layer, or combinations thereof.

22. A method of making a composition comprising a substrate, a non-fouling polymeric material, and optionally an undercoating layer immobilized on the substrate, the non-fouling polymeric material being covalently bound to the substrate or the undercoating layer, the method comprising imbibing one or more initiators into the substrate or the undercoating layer and grafting the non-fouling polymeric material from the imbibed substrate or the undercoating layer, wherein the one or more initiators is a redox initiator pair, wherein the redox initiator comprising a hydrophobic-hydrophilic initiator pair.

23. The method of claim 22, wherein the redox initiator system comprises a peroxide and a metal salt.

24. The method of claim 23, wherein the peroxide is dicumyl peroxide and the metal salt is Fe(II) gluconate.

* * * * *